United States Patent
Koizumi et al.

(10) Patent No.: US 11,730,722 B2
(45) Date of Patent: Aug. 22, 2023

(54) CORNEAL ENDOTHELIUM ECM THERAPEUTIC MEDICAMENTS

(71) Applicants: KYOTO PREFECTURAL PUBLIC UNIVERSITY CORPORATION, Kyoto (JP); THE DOSHISHA, Kyoto (JP); SENJU PHARMACEUTICAL CO., LTD., Osaka (JP)

(72) Inventors: Noriko Koizumi, Kyotanabe (JP); Naoki Okumura, Kyotanabe (JP); Shigeru Kinoshita, Kyoto (JP)

(73) Assignees: KYOTO PREFECTURAL PUBLIC UNIVERSITY CORPORATION, Kyoto (JP); THE DOSHISHA, Kyoto (JP); SENJU PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 14/907,881

(22) PCT Filed: Jul. 30, 2013

(86) PCT No.: PCT/JP2013/071095
§ 371 (c)(1),
(2) Date: Jan. 27, 2016

(87) PCT Pub. No.: WO2015/015654
PCT Pub. Date: Feb. 5, 2015

(65) Prior Publication Data
US 2016/0158210 A1 Jun. 9, 2016

(51) Int. Cl.
| | | |
|---|---|---|
| *A61K 31/4439* | (2006.01) | |
| *A61K 39/395* | (2006.01) | |
| *A61K 31/519* | (2006.01) | |
| *A61K 31/4725* | (2006.01) | |
| *A61K 31/4745* | (2006.01) | |
| *A61K 31/4709* | (2006.01) | |
| *A61K 31/4402* | (2006.01) | |
| *A61K 45/06* | (2006.01) | |
| *A61K 9/00* | (2006.01) | |
| *C12N 15/113* | (2010.01) | |

(52) U.S. Cl.
CPC ........ *A61K 31/4439* (2013.01); *A61K 9/0048* (2013.01); *A61K 31/4402* (2013.01); *A61K 31/4709* (2013.01); *A61K 31/4725* (2013.01); *A61K 31/4745* (2013.01); *A61K 31/519* (2013.01); *A61K 39/395* (2013.01); *A61K 45/06* (2013.01); *C12N 15/1136* (2013.01); *C12N 2310/14* (2013.01); *C12N 2320/30* (2013.01)

(58) Field of Classification Search
None
See application file for complete search history.

(56) References Cited

U.S. PATENT DOCUMENTS

| | | | | |
|---|---|---|---|---|
| 5,703,047 | A * | 12/1997 | Wilson | A61K 38/1833 424/491 |
| 2002/0115589 | A1* | 8/2002 | Nixon | A61K 38/57 514/8.9 |
| 2003/0166537 | A1 | 9/2003 | Hanke et al. | |
| 2003/0191137 | A1* | 10/2003 | Kim | A61K 31/497 514/255.05 |
| 2004/0038856 | A1 | 2/2004 | Chakravarty et al. | |
| 2006/0111375 | A1 | 5/2006 | Shimizu et al. | |
| 2007/0014767 | A1 | 1/2007 | Ezquerro Saenz et al. | |
| 2007/0142376 | A1 | 6/2007 | Fleenor et al. | |
| 2008/0194531 | A1 | 8/2008 | Steer et al. | |
| 2008/0267946 | A1* | 10/2008 | Kim | A61P 27/02 424/130.1 |
| 2009/0062247 | A1 | 3/2009 | Huang et al. | |
| 2010/0087486 | A1 | 4/2010 | Nakamura et al. | |
| 2010/0222280 | A1 | 9/2010 | Herrerías et al. | |
| 2010/0267731 | A1* | 10/2010 | Nakamura | A61K 9/0048 514/249 |
| 2012/0315256 | A1* | 12/2012 | Dotor De Las Herrerías | A61P 1/16 424/93.21 |

(Continued)

FOREIGN PATENT DOCUMENTS

| | | |
|---|---|---|
| JP | 2008-513465 A | 5/2008 |
| JP | 2008-533000 A | 8/2008 |
| JP | 2012-067097 A | 4/2012 |

(Continued)

OTHER PUBLICATIONS

Amin, Changes in Anterior Corneal Haze with Severity of Fuchs endothelial dystrophy, ARVO abstract, Jun. 2013.*
Elhalis et al., Fuchs Endothelial Corneal Dystrophy, Ocul Surf. Oct. 2010 ; 8(4): 173-184.*
Usui et al., Extracellular Matrix Production Regulation by TGF-j Corneal Endothelial Cells, Investigative Ophthalmology & Visual Science, Oct. 1998, vol. 39, No. 11.*
Okumura'2011, The New Therapeutic Concept of Using a Rho Kinase Inhibitor for the Treatment of Corneal Endothelial Dysfunction, Cornea 2011;30(Suppl. 1):S54-S59.*
Eghrari et al., Fuchs' corneal dystrophy, Expert Rev Ophthalmol. Apr. 2010 ; 5(2): 147-159 (Year: 2010).*

(Continued)

*Primary Examiner* — Blaine Lankford
(74) *Attorney, Agent, or Firm* — Leydig, Voit & Mayer, Ltd.

(57) ABSTRACT

The present invention provides medicaments for treating or preventing a disease, disorder, or condition associated with extracellular matrix (ECM) abnormality in a corneal endothelium, wherein the medicaments comprise a TGF-beta signal inhibiting agent. More specifically, this disease, disorder, or condition is a disorder associated with Fuchs' endothelial corneal dystrophy. Such a disorder includes photophobia, blurred vision, vision disorder, eye pain, lacrimation, hyperemia, pain, bullous keratopathy, ophthalmic unpleasantness, a decrease in contrast, glare, edema in corneal stroma, bullous keratopathy, corneal opacity, and the like. A preferable TGF-beta signal inhibiting agent includes 4-[4-(1,3-benzodioxol-5-yl)-5-(2-pyridinyl)-1H-imidazol-2-yl]benzamide.

9 Claims, 9 Drawing Sheets

(56) References Cited

U.S. PATENT DOCUMENTS

| | | |
|---|---|---|
| 2015/0044178 A1 | 2/2015 | Kinoshita et al. |
| 2016/0296505 A1 | 10/2016 | Koizumi et al. |

FOREIGN PATENT DOCUMENTS

| | | | |
|---|---|---|---|
| JP | 2013520405 A | 6/2013 | |
| JP | 6403217 B2 | 10/2018 | |
| RU | 2232771 C2 | 5/2003 | |
| WO | WO 2006/031931 A2 | 3/2006 | |
| WO | WO 2006/096011 A | 9/2006 | |
| WO | WO 2009/146408 A1 | 12/2009 | |
| WO | 2011101478 A1 | 8/2011 | |
| WO | WO 2012/009171 * | 1/2012 | ........... A61K 31/122 |
| WO | WO 2012/009171 A2 | 1/2012 | |
| WO | WO 2012/073238 A1 | 6/2012 | |
| WO | WO 2013/086236 A2 | 6/2013 | |
| WO | 2013100208 A1 | 7/2013 | |
| WO | WO 2015/015654 A1 | 2/2015 | |

OTHER PUBLICATIONS

Connolly et al., Complexities of TGF-β Targeted Cancer Therapy, Intteerrnattiionall Jourrnall off Biiollogiiccall Scciieenccees, 2012; 8(7):964-978. doi: 10.7150/ijbs.4564 (Year: 2012).*

Zhu et al., A Novel Aptamer Targeting TGF-b Receptor II Inhibits Transdifferentiation of Human Tenon's Fibroblasts into Myofibroblast, Investigative Ophthalmology & Visual Science, Oct. 2012, vol. 53, No. 11 (Year: 2011).*

Zhao et al, Inhibition of Transforming Growth Factor-1-induced Signaling and Epithelial-to-Mesenchymal Transition by the Smad-binding Peptide Aptamer Trx-SARA, Molecular Biology of the Cell vol. 17, 3819-3831, Sep. 2006 (Year: 2006).*

Kang et al., Combinatorial selection of a single stranded DNA thioaptamer targeting TGF-b1 protein, Bioorganic & Medicinal Chemistry Letters 18 (2008) 1835-1839 (Year: 2008).*

Cui et al., Selective inhibition of TGF-b responsive genes by Smad-interacting peptide aptamers from FoxH1, Lef1 and CBP, Oncogene (2005) 24, 3864-3874 (Year: 2005).*

Sakamoto et al., Blockade of TGF-beta by in vivo gene transfer of a soluble TGF-beta type II receptor in the muscle inhibits corneal opacification, edema and angiogenesis, Gene Therapy 7(22):1915-1924. (2000).

Okumura et al., Inhibition of TGF-beta Signaling Enables Human Corneal Endothelial Cell Expansion In Vitro for Use in Regenerative Medicine, PLoS ONE 8(2): e58000. (2013).

Koizumi, Development of new therapeutic modalities for corneal endothelial disease using somatic stem cells, Journal of Clinical and Experimental Medicine, 241(10): 765-770. (2012).

Ho et al., Cell Line of Fuchs' Corneal Dystrophy Produces an Abnormal Extracellular Matrix, The Association for Research in Vision and Ophthalmology, Meeting Abstract. (Mar. 12, 2013).

Ho et al., Cell Line of Fuchs' Corneal Dystrophy Produces an Abnormal Extracellular Matrix, The Association for Research in Vision and Ophthalmology, Poster Presentation. (May 6, 2013).

Koizumi et al., "Development of new therapeutic modalities for corneal endothelial disease focused on the proliferation of corneal endothelial cells using animal models," *Exp. Eye. Res.*, 95(1): 60-67 (2012).

Russian Patent Office, Official Action in Russian Patent Application No. 2016106641 (dated Jun. 20, 2017).

Russian Patent Office, Search Report in Russian Patent Application No. 2016106641 (dated Jun. 20, 2017).

Russian Patent Office, Decision of Refusal in Russian Patent Application No. 2016106641 (dated Aug. 16, 2018).

Okumura et al., "Activation of TGF-β signaling induces cell death via the unfolded protein response in Fuchs endothelial corneal dystrophy," *Sci. Rep.*, 7(1): 6801 (2017).

Shea, "Anatomy and Physiology of the Eye," Certified Patient Service Specialist Distance Learning Course, pp. 1-21 (BSM Consulting 2010-2012).

Smith, "Nutrition and Eye Diseases," *Journal of Orthomolecular Medicine*, 25(2): 67-76 (2010).

ZHU et al.,"Eye Anatomy," *eLS*, DOI: 10.1002/9780470015902.a0000108.pub2 (2012).

Japanese Patent Office, Official Action in Japanese Patent Application No. 2015-529317 (dated Mar. 14, 2018).

Yu et al., "Concentration change of TGF-β1 in aqueous humor of rabbits," *Asian Pac. J. Trop. Med.*, 7(3): 241-243 (2014).

Japanese Patent Office, Office Action in Japanese Patent Application No. 2015-545338 (dated Jan. 22, 2019).

Russian Patent Office, Office Action in Russian Patent Application No. 2019107381 (dated Mar. 19, 2019).

Russian Patent Office, Notification on the Results of Invention Patentability Assessment in Russian Patent Application No. 2016121150 (dated Jan. 22, 2019).

Mexican Patent Office, Office Action in Mexican Patent Application No. MX/a/2016/005680 (dated May 22, 2019).

Mexican Patent Office, Office Action in Mexican Patent Application No. MX/a/2016/001457 (dated Mar. 25, 2019).

Ashaye et al., "Pattern of Corneal Opacity in Ibadan, Nigeria," *Ann. Afr. Med.*, 3(4): 185-187 (2004).

Zou et al., "Keratorefractive surgery and glaucoma," *Int. J. Opthalmol.*, 1(3): 189-194 (2008).

Canadian Patent Office, Examination Report in Canadian Patent Application No. 2,919,316 (dated May 7, 2019).

Goodman et al., "Conjunctivitis," *The Journal of the American Medical Association*, 309(20): 2176 (2013).

Hao et al., "In Vivo Structure Activity Relationship Study of Dorsomorphin Analogs Identifies Selective VEGF and BMP Inhibitors," *ACS Chem. Biol.*, 5(2): 245-253 (2010).

Huang et al., "A Hierarchy of Endothelial Colony-Forming Cell Activity Displayed by Bovine Corneal Endothelial Cells," *Invest. Ophthalmol. Vis. Sci.*, 51(8): 3943-3949 (2010).

Jinnin et al., "Characterization of SIS3, a Novel Specific Inhibitor of Smad3, and Its Effect on Transforming Growth Factor-β1-Induced Extracellular Matrix Expression," *Mol. Pharmacol.*, 69(2): 597-607 (2006).

Joyce et al., "Proliferative Capacity of Corneal Endothelial Cells," *Exp. Eye Res.*, 95(1): 16-23 (2012).

Kim et al., "Lithium treatment increases endothelial cell survival and autophagy in a mouse model of Fuchs endothelial Corneal dystrophy," *The British Journal of Opthalmology*, 97(8) : 1068-1073 (2013).

MCCAA, "The Eye and Visual Nervous System: Anatomy, Physiology and Toxicology," *Environmental Health Perspectives*, 44: 1-8 (1982).

Motegi et al., "Regulation of bovine corneal endothelial cell cycle by transforming growth factor-β," *Acta Ophthalmol. Scand.*, 81(5): 517-525 (2003).

Tsukasaki et al., "Nephronectin expression is regulated by SMAD signaling in osteoblast-like MC3T3-E1 cells," *Biochem. Biophys. Res. Common.*, 425(2): 390-392 (2012).

Ueda et al., "Protective effects of TGF-beta inhibitors on retinal blood vessels in the injured rat retina," *J. Pharmacol. Sci.*, 115(Suppl. 1): Abstract 262P (2011).

Uhl et al., "SD-208, a Novel Transforming Growth Factor β Receptor I Kinase Inhibitor, Inhibits Growth and Invasiveness and Enhances Immunogenicity of Murine and Human Glioma Cells In vitro and In vivo," *Cancer Res.*, 64(21): 7954-7961 (2004).

European Patent Office, Extended European Search Report in European Patent Application No. 14857909.7 (dated Jun. 16, 2017).

European Patent Office, Communication Pursuant to Article 94(3) EPC in European Patent Application No. 14857909.7 (dated Sep. 26, 2018).

Japanese Patent Office, International Search Report in International Patent Application No. PCT/JP2014/079513 (dated Feb. 10, 2015).

Japanese Patent Office, Official Action in Japanese Patent Application No. 2015-545338 (dated Jul. 17, 2018).

Russian Patent Office, Official Action in Russian Patent Application No. 2016121150 (dated Aug. 20, 2018).

(56) References Cited

OTHER PUBLICATIONS

Russian Patent Office, Search Report in Russian Patent Application No. 2016121150 (dated Jul. 31, 2018).
Brazilian Patent Office, Preliminary Office Action in Brazilian Patent Application No. BR112016009493-0 (dated Sep. 24, 2019).
European Patent Office, Communication Pursuant to Article 94(3) EPC in European Patent Application No. 14857909.7 (dated Sep. 3, 2019).
Mexican Patent Office, Office Action in Mexican Patent Application No. MX/a/2016/005680 (dated Sep. 17, 2019).
Brazilian Patent Office, Office Action in Brazilian Patent Application No. BR112016002015-4 (dated Oct. 1, 2019).
Mexican Patent Office, Office Action in Mexican Patent Application No. MX/a/2016/001457 (dated Oct. 17, 2019).
Laping et al., "Inhbition of Transforming Growth Factor (TGF)-β1-Induced Extracellular Matrix with a Novel Inhibitor of the TGF-β Type I Receptor Kinase Activity: SB-431542," *Mol. Phamacol.*, 62(1): 58-64 (2002).
Climo et al., "Comparison of the in-vitro and in-vivo efficacy of FK037, vancomycin, imipenem and nafcillin against staphylococcal species," *J. Antimicrob. Chemother.*, 40(1): 59-66 (1997).
Den Hollander et al., "Comparison of Pharmacodynamics of Azithromycin and Erythromycin In Vitro and In Vivo," *Antimicrob. Agents Chemother.*, 42(2): 377-382 (1998).
Rodriguez et al., "In vitro and in vivo comparison of the anti-staphylococcal efficacy of generic products and the innovator of oxacillin," *BMC Infect. Dis.*, 10: 153 (2010).
Wang et al., "The impact of early ADME profiling on drug discovery and development strategy," *Drug Discovery World*, Fall 2004: 73-86 (2004).
Canadian Intellectual Property Office, Office Action in Canadian Patent Application No. 2,927,898 (dated Dec. 9, 2020).
Mexican Patent Office, Office Action in Mexican Patent Application No. MX/a/2016/001457 (dated Jul. 13, 2020).
Mexican Patent Office, Office Action in Mexican Patent Application No. MX/a/2016/005680 (dated Jul. 13, 2020).
Matthaei et al., "Endothelial Cdkn1a (p21) Overexpression and Accelerated Senescence in a Mouse Model of Fuchs Endothelial Corneal Dystrophy," *Invest. Ophthalmol. Vis. Sci.*, 53(10): 6718-6727 (2012).
Canadian Patent Office, Examination Report in Canadian Patent Application No. 2,919,316 (dated May 28, 2020).
Japanese Patent Office, Office Action in Japanese Patent Application No. 2015-545338 (dated Feb. 4, 2020).
European Patent Office, Extended European Search Report in European Patent Application No. 20195546.5 (dated Mar. 17, 2021).
Engler et al., "Unfolded protein response in Fuchs Endothelial Corneal Dystrophy: a Unifying Pathogenic Pathway?" *Am. J. Ophthalmol.*, 149(2): 194 (2010).
Park et al., "The chemical chaperone 4-phenylbutyric acid attenuates pressureoverload cardiac hypertrophy by alleviating endoplasmic reticulum stress," *Biochem. Biophys. Res. Commun.*, 421(3): 578-584 (2012).
Japanese Patent Office, Decision of Refusal in Japanese Patent Application No. 2019-197763 (dated Jul. 14, 2021).
Brazilian National Institute of Industrial Property, Unfavorable Opinion in Brazilian Patent Application No. BR112016002015-4 (Apr. 27, 2022).
Russian Federal Service for Intellectual Property, Official Action in Russian Patent Application No. 2019107381/04(014267) (dated Mar. 9, 2022).
Russian Federal Service for Intellectual Property, Search Report in Russian Patent Application No. 2019107381/04(014267) (dated Mar. 9, 2022).
Russian Federal Service for Intellectual Property, Official Action in Russian Patent Application No. 2019107381/04(014267) (dated Jul. 26, 2022).
Ashaye et al., "Pattern of Corneal Opacity in Ibadan, Nigeria," *Annals of African Med.*, 3(4): 185-187 (2004).
Chen et al., "TGF-β2 in Aqueous Humor Suppresses S-Phase Entry in Cultured Corneal Endothelial Cells," *Invest. Ophthalmol. Vis. Sci.*, 40(11): 2513-19 (1999).
Iskeleli et al., "Richner-Hanhart Syndrome (Tyrosinemia Type Ii): A Case Report of Delayed Diagnosis with Pseudodendritic Corneal Lesion," *Turkish J. Peds.*, 53: 692-694 (2011).
Shoaib, "Features, Causes and Prevention of Toxic Anterior Segment Syndrome (TASS)—An Outbreak Investigation," *Pak. J. Ophthalmol.*, 29(2): 100-105 (2013).
Van De Pol et al., "Objective Assessment of Transient Corneal Haze and Its Relation to Visual Performance After Photorefractive Keratectomy," *Am. J. Ophthalmol.*, 132(2): 204-210 (2001).
Wipperman et al., "Evaluation and Management of Corneal Abrasions," *Am. Fam. Physician*, 87(2): 114-120 (2013).
Zou et al., "Keratorefractive Surgery and Glaucoma," *Int. J. Ophthalmol.*, 1(3): 189-194 (2008).
Brazillian National Institute of Industrial Property, Office Action in Brazilian Patent Application No. BR122022015697-5 (dated Dec. 19, 2022).
Japan Patent Office, Notice of Reasons for Refusal in Japanese Patent Application No. 2021-168205 (dated Dec. 16, 2022).
Russian Federal Service for Intellectual Property, Official Action in Russian Patent Application No. 2019107381/04 (dated Feb. 9, 2023).
Brazilian National Institute of Industrial Property, Office Action in Brazilian Patent Application No. BR112016002015-4 (dated Sep. 20, 2022).
Russian Patent Office, Minutes of Interview in Russian Patent Application No. 2016121150 (Aug. 12, 2019).
U.S. Appl. No. 15/031,183, filed Apr. 21, 2016.
U.S. Appl. No. 17/831,843, filed Jun, 3, 2022.

* cited by examiner

CORNEAL ENDOTHELIUM ECM THERAPEUTIC MEDICAMENTS

TECHNICAL FIELD

The present invention is related to techniques, methods, agents, and the like to treat or prevent a disease, disorder, or condition associated with extracellular matrix (ECM) abnormality in a corneal endothelium.

BACKGROUND ART

Visual information is recognized when light transmitted into the cornea, which is a transparent tissue at the frontmost part of an eye ball, reaches the retina and excites nerve cells of the retina and a generated electric signal is transmitted through the optic nerve to the visual cortex of the cerebrum. To attain good vision, it is necessary that the cornea is transparent. The transparency of the cornea is maintained by maintaining constant water content with pumping and barrier functions of corneal endothelial cells.

Human corneal endothelial cells are present at a density of about 3000 per 1 $mm^2$ at birth. However, once damaged, the ability of the cells to regenerate is highly limited. Fuchs' endothelial corneal dystrophy is a disease in which an abnormality occurs in the endothelial cells inside of the cornea to cause edema of the cornea and the like. The cause thereof is unknown. In Fuchs' endothelial corneal dystrophy, an extracellular matrix, such as collagen and the like, deposits on one part of the back surface of Descemet's membrane at the back side of the cornea to cause corneal guttae and thickening of Descemet's membrane. Corneal guttae and thickening of Descemet's membrane are causes of photophobia and blurred vision in Fuchs' endothelial corneal dystrophy patients and significantly impair the QOL of the patients. For Fuchs' endothelial corneal dystrophy, there is considered no effective therapeutic method other than keratoplasty. However, cornea donation is insufficient in Japan. While there are about 2600 patients waiting for keratoplasty, the number of keratoplasty cases performed domestically is about 1700 annually.

With regard to Fuchs' endothelial corneal dystrophy, culture of corneal endothelial cells derived from Fuchs' endothelial corneal dystrophy patients (Non Patent Literatures 1 and 3) as well as immobilization thereof (Non Patent Literatures 2) were reported, while a suitable cell for screening for a therapeutic medicament and an advance-preventing medicament that keeps characteristics of the disease, such as accompanying overproduction of a extracellular matrix, is not reported. Accordingly, there is a limit on development of the therapeutic medicament. Currently, there is no therapeutic medicament clinically used, and keratoplasty has to be relied on.

In addition, Patent Literature 1 discloses a TGF-beta1 inhibitor peptide to perform therapy against corneal fibrosis and/or opacity. Patent Literature 2 discloses antibodies that bind to TGF-beta1, 2, or 3. Patent Literature 3 discloses that an Nrf2 agonist or activator may be used in therapy against corneal endothelial disorder. Patent Literature 4 discloses a peptide that can bind to a transforming growth factor TGF-beta1 and become a strongly inhibiting agent against the bioactivity of TGF-beta1 by direct binding with a cytokine. Patent Literature 5 discloses a scar-formation suppressing agent including BMP-7 polypeptide. Patent Literature 6 generally describes a corneal disorder as a disease against which the TGF-beta inhibitory effect is therapeutically or preventively effective.

CITATION LIST

Patent Literature

[PTL 1] Japanese National Phase PCT Laid-Open Publication No. 2013-520405
[PTL 2] International Publication No. WO 2012/167143 pamphlet
[PTL 3] International Publication No. WO 2012/009171 pamphlet
[PTL 4] Japanese National Phase PCT Laid-Open Publication No. 2007-525204
[PTL 5] Japanese National Phase PCT Laid-Open Publication No. 2006-508169
[PTL 6] International Publication No. WO 2004/018430 pamphlet

Non Patent Literature

[NPL 1] Zaniolo K, et al., Exp. Eye Res. Vol. 94(1):22-31, 2012.
[NPL 2] Azizi B, et al., Invest Ophthalmol Vis. Sci. 2; 52(13):9291-9297, 2011.
[NPL 3] Kelliher C. et al., Exp. Eye Res. Vol. 93(6), 880-888, 2011.

SUMMARY OF INVENTION

Solution to Problem

The inventors have found that the inhibition of a transforming growth factor-beta (TGF-beta) pathway can suppress the deposition of an extracellular matrix (ECM) such as collagen and the like, as seen in Fuchs' endothelial corneal dystrophy and the like; have found techniques that can treat or prevent a ECM-associated disorder; and have completed the present invention. Accordingly, the invention of the present application provides those inventions as follows:

(1) A medicament for treating or preventing a disease, disorder, or condition associated with extracellular matrix (ECM) abnormality in a corneal endothelium, wherein the medicament comprises a TGF-beta signal inhibiting agent.
(2) The medicament for treating or preventing according to item 1, wherein the disease, disorder, or condition is a disorder related to Fuchs' endothelial corneal dystrophy.
(3) The medicament for treating or preventing according to item 1 or 2, wherein the disease, disorder, or condition comprises at least one selected from the group consisting of photophobia, blurred vision, vision disorder, eye pain, lacrimation, hyperemia, pain, bullous keratopathy, ophthalmic unpleasantness, a decrease in contrast, glare, edema in corneal stroma, bullous keratopathy, and corneal opacity in Fuchs' endothelial corneal dystrophy.
(4) The medicament for treating or preventing according to any one of items 1 to 3, wherein the TGF-beta signal inhibiting agent comprises at least one of 4-[4-(1,3-benzodioxol-5-yl)-5-(2-pyridinyl)-1H-imidazol-2-yl]benzamide, BMP-7, anti-TGF-beta antibody, anti-TGF-beta receptor antibody, siRNA of TGF-beta, siRNA of a TGF-beta receptor, shRNA of TGF-beta, shRNA of a TGF-beta receptor, an aptamer of TGF-beta, an aptamer of a TGF-beta receptor, an antisense oligonucleotide of TGF-beta, 6,7-dimethoxy-2-

((2E)-3-(1-methyl-2-phenyl-1H-pyrrolo[2,3-b]pyridin-3-yl-prop-2-enoyl))-1,2,3,4-tetrahydroisoquinolone, 3-(6-methyl-2-pyridinyl)-N-phenyl-4-(4-quinolinyl)-1H-pyrazole-1-carbothioamide, 2-(3-(6-methylpyridin-2-yl)-1H-pyrazol-4-yl)-1,5-naphthyridine, 6-(4-(piperidin-1-yl)ethoxy)phenyl)-3-(pyridin-4-yl)pyrazolo[1,5-a]pyrimidine, 2-(5-chloro-2-fluorophenyl)-4-[(4-pyridinyl)amino]pteridine, 4-[3-(2-pyridinyl)-1H-pyrazol-4-yl]-quinoline, pharmaceutically acceptable salts or solvates thereof, or solvates of the pharmaceutically acceptable salts.

(5) The medicament for treating or preventing according to any one of items 1 to 4, wherein the TGF-beta signal inhibiting agent comprises 4-[4-(1,3-benzodioxol-5-yl)-5-(2-pyridinyl)-1H-imidazol-2-yl]benzamide or a pharmaceutically acceptable salt thereof.

(6) The medicament for treating or preventing according to any one of items 1 to 5, wherein the corneal endothelium is of a primate.

(7) The medicament for treating or preventing according to any one of items 1 to 6, wherein the corneal endothelium is of a human.

(8) The medicament for treating or preventing according to any one of items 1 to 7, comprising an additional medicinal component.

(9) The medicament for treating or preventing according to any one of items 1 to 8, being eye-drops.

(10) A TGF-beta signal inhibitory substance for treatment or prevention of a disorder associated with extracellular matrix (ECM) abnormality in a corneal endothelium.

(10A) The TGF-beta signal inhibitory substance according to (10), wherein the TGF-beta signal inhibitory substance has a characteristic of the inhibiting agent according to any one of (1) to (9).

(11) A method for treating or preventing a disorder associated with extracellular matrix (ECM) abnormality in a corneal endothelium in a subject, wherein the method comprises a step of administering an effective amount of a TGF-beta signal inhibiting agent to the subject.

In the present invention, in addition to the clarified combinations, the above-mentioned one or more characteristics are intended as being further combined and provided. Still further embodiments and advantages according to the present invention will be recognized by those skilled in the art upon reading and understanding the following the Detailed Description of the Invention as necessary.

Advantageous Effects of Invention

The present invention provides a medicament that can treat or prevent a disease associated with extracellular matrix (ECM) abnormality such as Fuchs' endothelial corneal dystrophy, for which only one therapeutic method is conventionally keratoplasty, as well as a technique that can realize eye-drops and the like thereof.

BRIEF DESCRIPTION OF DRAWINGS

FIG. 1 shows a result of analyzing, by real-time PCR, the expression amount of a gene related to epithelial-mesenchymal transition (EMT) related to production of an extracellular matrix. The iFCED was used which was obtained by obtaining and culturing corneal endothelial cells from three patients that led to bullous keratopathy by clinical diagnosis of Fuchs' endothelial corneal dystrophy and underwent Descemet membrane endothelial keratoplasty (DMEK) under the written consent and the approval of Ethics Committee. SV40 and hTERT genes were introduced by lentivirus to the cultured corneal endothelial cells derived from a Fuchs' endothelial corneal dystrophy patient to make an immobilized strain. Corneal endothelial cells cultured from a cornea for research imported as a control from a Seattle eye bank were immobilized by a similar method to make an immobilized cell strain (iHCEC). For the iHCEC and the iFECD, maintenance culture was performed in DMEM+10% FBS. In each graph, the left shows iHCEC, and the right shows iFECD. The A shows relative expression of Snail1, the B shows relative expression of Snail2, and the C shows relative expression of ZEB1. By real-time PCR, the significant promotion of expression of Snail1 and ZEB1 was recognized in the iFECD in comparison with the iHCEC.

FIG. 2 shows a result of stimulation by TGF-beta, which is known to accelerate expression of Snail1 and ZEB1, in order to confirm whether the expression promotion of Snail1 and ZEB1 relates to production of an extracellular matrix. The white shows iHCEC and the black shows iFECD. The A shows the relative expression of Snail1, the B shows the relative expression of ZEB1, the C shows the relative expression of collagen type I, the D shows the relative expression of collagen type IV, the E shows the relative expression of collagen type VIII, and the F shows the relative expression of Fibronectin. TGF-beta was confirmed to significantly accelerate expression of Snail1 and ZEB1 in iFECD (A, B). Then, when the gene expression amount of an extracellular matrix-constituting protein was analyzed by real-time PCR, the expression of collagen type I, collagen type IV, collagen type VIII, and Fibronectin was significantly accelerated.

FIG. 3 shows a result of examining whether an extracellular matrix produced by the iFECD is accelerated by TGF-beta. The iHCEC and the iFECD were cultured in DMEM on Transwell without serum, one week after which they were fixed in a confluent state and HE-stained (The left panel shows photomicrographs of HE staining, the upper row shows iHCEC, and bottom row shows iFECD. The left side shows controls and the right side shows a result of TGF-beta stimulation). The right graph shows measurement values of thickness. In the graph, the left side shows a control, the right side shows a result of stimulation by TGF-beta, the white shows iHCEC, and the black shows iFECD. * and # each show the statistical significance of each other when $p<0.05$. With regard to the iHCEC and iFECD, it was recognized that the TGF-beta stimulation produced a significantly thickened extracellular matrix. Further, it was recognized that in the presence of TGF-beta, the iFECD produced a significantly thickened extracellular matrix in comparison with the iHCEC. The above description shows that in corneal endothelial cells of a Fuchs' endothelial corneal dystrophy patient, the expression level of Snail1 and ZEB1 is high and that the production quantity of an extracellular matrix in response to the TGF-beta stimulation is significantly higher than corneal endothelial cells of a healthy subject.

FIG. 4 shows a result of examining an effect on the extracellular matrix production by suppression of Snail1 and ZEB1 using siRNA in order to demonstrate that the expression promotion of Snail1 and ZEB1 causes production of an extracellular matrix. The white shows iHCEC and the black shows iFECD. The A to E show a result of Snail1 siRNA and the F to J show a result of Snail1 siRNA. The A shows a result of ZEB1, the F shows a result of SNAIL', the B and G show a result of collagen type I, the C and H show a result of collagen type IV, the D and I show a result of collagen type VIII, and the E and J show a result of Fibronectin. * shows statistical significance when p<0.01. It was confirmed that siRNA suppresses expression of Snail1 and ZEB1 (A, F). Expression suppression of Snail1 or ZEB1 by siRNA significantly suppresses expression of collagen type I, collagen type IV, collagen type VIII, and Fibronectin.

FIG. 5 shows a result of examining expression of collagen type I, collagen type IV, and Fibronectin by immunostaining in a similar manner. The left side shows a result of control siRNA, the middle shows a result of ZEB siRNA, and the right side shows a result of SNAIL1 siRNA. Two upper rows show collagen type I, two middle rows show collagen type IV, two lower rows show Fibronectin. Each upper row of the pairs of two rows shows iHCEC and each lower row thereof shows iFECD. It was confirmed that expression suppression of Snail1 or ZEB1 by siRNA also suppresses expression of collagen type I, collagen type IV, collagen type VIII, and Fibronectin at a protein level.

FIG. 6 further shows a result of culturing the iHCEC and the iFECD in DMEM on Transwell without serum, and one week later fixing them in a confluent state and HE-staining (The left panel shows a photomicrograph of HE-staining, the upper row shows iHCEC, and the lower row shows iFECD. The left side shows a result of a siRNA control, the middle shows a result of siRNA ZEB1, and the right side shows a result of siRNA SNAIL). The right graph shows measurement values of thickness. In the graph, the left side shows a siRNA control, the middle shows siRNA ZEB1, the right side shows a result of stimulation by siRNA SNAIL, the white shows iHCEC, and the black shows iFECD. * shows the statistical significance when p<0.01. Expression suppression of Snail1 or ZEB1 by siRNA suppressed extracellular matrix overproduction in the iFECD to result in the normal level.

FIG. 7 shows a result of inhibiting TGF-beta signal with a TGF-beta signal inhibiting agent SB431542 (0 µM, 1 µM, 3 µM, and 10 µM). The white shows iHCEC and the black shows iFECD. The A shows a result of Snail1, the B shows a result of ZEB1, the D shows collagen type I, the E shows collagen type IV, the F shows collagen type VIII, the G shows Fibronectin. * shows the statistical significance when p<0.01. As a result of the TGF-beta signal inhibition, it was recognized by real-time PCR that the expression amount of Snail1 and ZEB1 was significantly decreased. Further, when the gene expression amount of an extracellular matrix-constituting protein in the iFCED was analyzed with SB431542 by real-time PCR, the expression of collagen type I, collagen type IV, collagen type VIII, and Fibronectin was significantly suppressed.

FIG. 8 shows a result of examining expression of collagen type I, collagen type IV, and Fibronectin by immunostaining, similarly as in FIG. 7. The left side shows a result of a control and the right side shows a result of stimulation by SB431542. Two upper rows show collagen type I, two middle rows show collagen type IV, and two lower rows show Fibronectin. Each upper row of the pairs of two rows shows iHCEC and each lower row thereof shows iFECD. It was confirmed that TGF-beta signal inhibition using SB431542 also suppresses expression of collagen type I, collagen type IV, collagen type VIII, and Fibronectin in a protein level.

FIG. 9 further shows a result of culturing the iHCEC and iFECD in DMEM on Transwell without serum, and one week later fixing them in a confluent state and HE-staining (In the left panel, the upper row shows iHCEC, and the bottom row shows iFECD. The left side shows a control and the right side shows a result of stimulation by SB431542). The right graph shows measurement values of thickness. The left side shows a control, the right side shows a result of stimulation by SB431542, the white shows iHCEC, and the black shows iFECD. * is the statistical significance when p<0.01. TGF-beta signal inhibition using SB431542 suppressed extracellular matrix overproduction of iFECD to result in the normal level.

DESCRIPTION OF EMBODIMENTS

Figure 1:
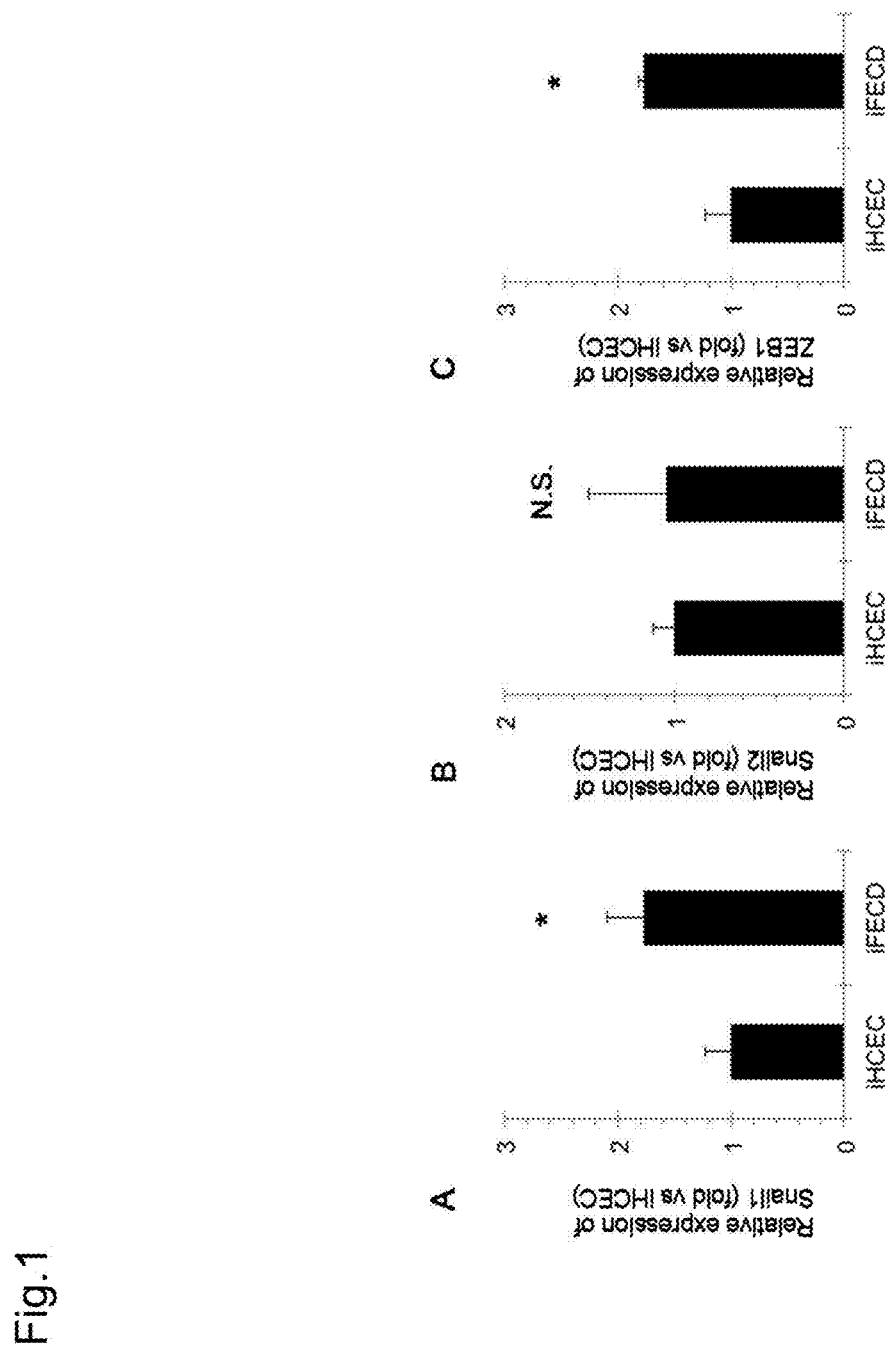
FIG. 1 shows a state that expression of Snail1 and ZEB1 in corneal endothelial cells derived from a Fuchs' endothelial corneal dystrophy patient is promoted.

The present invention is described hereinafter. Throughout the entire specification, a singular expression should be understood as encompassing the concept thereof in the plural form unless specifically noted otherwise. Thus, singular articles (e.g., "a", "an", "the" and the like in case of English) should also be understood as encompassing the concept thereof in the plural form unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the terms commonly understood by those skilled in the art to which the present invention pertains. In case of a contradiction, the present specification (including the definitions) takes precedence.

Definition

As used herein, "iFECD" (immobilized or immortalized Fuchs' endothelial corneal dystrophy) is an abbreviation for an immobilized cell of Fuchs' endothelial corneal dystrophy.

As used herein, "HCEC" (human corneal endothelial cells) is an abbreviation for human corneal endothelial cells. "iHCEC" is an abbreviation for immobilized (or immortalized) human corneal endothelial cells.

As used herein, "transforming growth factor-beta (transforming growth factor-beta; also referred to as an abbreviated name TGF-beta)" is used with the meaning similar to the meaning of those used in the art; and the transforming growth factor-beta is a homodimer multifunctional cytokine of a molecular weight of 25 kD, which exhibits various types of biological activity. TGF-beta has a role in pathogenesis of a variety of sclerosing diseases, rheumatoid arthritis, and proliferative vitreoretinopathy, and is greatly involved in hair loss, suppressing the action of immunocompetent cells, suppressing overproduction of protease to prevent lung tissues from being degraded and preventing emphysema, and suppressing the growth of cancer cells, and the like. Three isoforms of TGF-beta exist in humans, namely TGF-beta1 to beta3. TGF-beta is produced as an inactive latent type with a molecular weight of about 300 kD, which is not able to bind to a receptor. TGF-beta is activated on a target cell surface or in the periphery thereof to become an active type capable of binding to a receptor, thus exerting the action thereof.

Although it is not desired to be restricted by theories, the action of TGF-beta in a target cell is regarded as being transmitted by a phosphorylation pathway of a set of proteins for performing information transmission, referred to as Smad. First, when active TGF-beta is bound to a type II TGF-beta receptor present on a surface of a target cell, a receptor complex is formed which consists of two molecules of a type II receptor and two molecules of a type I TGF-beta receptor, and the type II receptor phosphorylates the type I receptor. Next, the phosphorylated type I receptor phosphorylates Smad2 or Smad3, and the phosphorylated Smad2 or Smad3 forms a complex with Smad4, and the complex transfers to a nucleus, binds to a target sequence referred to as CAGA box, which is present in a target gene promoter region, and induces transcriptional expression of a target gene together with a coactivator.

The transforming (transformation) growth factor-beta (TGF-beta) signal transduction pathway is capable of regulating many cell activities, such as cell growth and differentiation, growth arrest, apoptosis, and epithelial-to-mesenchymal conversion (EMT), by regulation of a target gene thereof. TGF-beta family members, including the TGF-beta itself (such as TGF-beta 1, TGF-beta 2 and TGF-beta 3), activin and bone morphogenic protein (BMP), are strong regulating agents for cell growth, differentiation, migration and apoptosis.

The TGF-beta is a protein of about 24 kD, which is produced by many cells including B lymphocyte, T lymphocyte and activated macrophage, and by many other cell types. Effects of TGF-beta to immune systems include IL-2 receptor induction, inhibition of IL-1 induced thymic cell growth, and blocking of IFN-gamma-induced macrophage activation. The TGF-beta is thought to be involved in a variety of pathological conditions (Border et al., (1992) J. Clin. Invest. 90:1), and is sufficiently supported to function as either a tumor inhibitory substance or a tumor promoter.

TGF-beta mediates the signaling thereof by two serine/threonine kinase cell surface receptors, TGF-betaRII and ALK5. TGF-beta signaling is initiated by ligand-induced receptor dimerization, which allows TGF-betaRII to phosphorylate an ALK5 receptor. The phosphorylation thereof is such that ALK5 kinase activity is activated and the activated ALK5 then phosphorylates a downstream effector Smad protein (vertebrate homologue of MAD or "Mothers against DPP (decapentaplegic)" protein), Smad2 or 3. The p-Smad2/3 complex with Smad4 enters a nucleus to activate the transcription of a target gene.

Smad3 is a member of an R-Smad (receptor-activated Smad) subgroup of Smad, and is a direct mediator of activation of transcription by a TGF-beta receptor. TGF-beta stimulation causes phosphorylation and activation of Smad2 and Smad3, which forms a complex with Smad4 ("common Smad" or "co-Smad" in vertebrates), which is accumulated together with a nucleus to regulate the transcription of a target gene. R-Smad is localized at a cytoplasm, and forms a complex with a co-Smad through ligand-induced phosphorylation by a TGF-beta receptor; and the complex moves to a nucleus, which then regulates gene expression that is associated with chromatin and a cooperative transcription factor. Smad6 and Smad7 are each inhibitory Smad ("I-Smad"), that is, they are transcriptionally induced by TGF-beta and function as an inhibiting agent for TGF-beta signaling (Feng et al., (2005) Annu. Rev. Cell. Dev. Biol. 21:659). Smad6/7 inhibits the receptor-mediated activation of R-Smad to exert their inhibitory effect; and they are associated with a type I receptor, which competitively prevents mobilization and phosphorylation of R-Smad. Smad6 and Smad7 are known to replenish E3 ubiquitin ligase, which causes ubiquitination and degradation of Smad6/7 interactive protein.

With regard to the TGF-beta signal transduction pathway, another pathway additionally exists which is transmitted by BMP-7 or the like, which is regarded as exhibiting functions via ALK-1/2/3/6 and then via Smad1/5/8. With regard to the TGF-beta signal transduction pathway, also see J. Massagu'e, Annu. Rev. Biochem. 1998. 67: 753-91; Vilar J M G, Jansen R, Sander C (2006) PLoS Comput Biol 2(1):e3; Leask, A., Abraham, D. J. FASEB J. 18, 816-827 (2004); Coert Margadant & Arnoud Sonnenberg EMBO reports (2010) 11, 97-105; Joel Rosenbloom et al., Ann Intern Med. 2010; 152: 159-166 and the like.

As used herein, "transforming growth factor (TGF)-beta signal inhibiting agent" refers to any factor that inhibits TGF signaling. When TGF-beta is counteracted, the agent responsible may be referred to as an antagonist. However, in the case of the present invention, the TGF-beta antagonist is encompassed by the TGF-beta signal inhibiting agent. Since this inhibiting agent is commonly a substance, a "TGF-beta signal inhibitory substance" may be interchangeably used with a "TGF-beta signal inhibiting agent".

Figure 3:
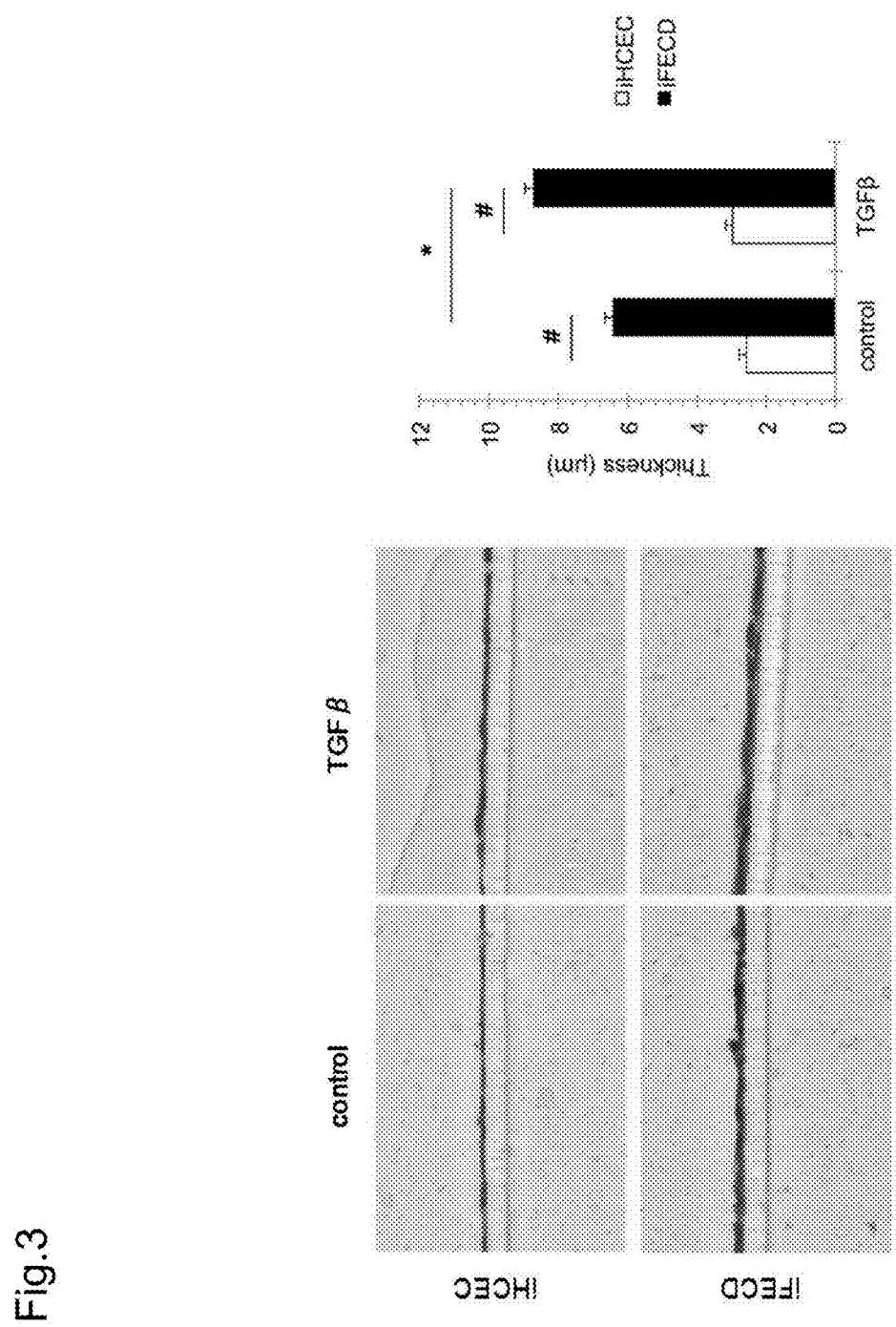
FIG. 3 shows a state that TGF-beta accelerates protein production in an in vitro matrix-constituting protein evaluation model.

Therefore, the TGF-beta signal inhibiting agent used in the present invention typically includes, without limitation, an antagonist of TGF-beta, an antagonist of a receptor of TGF-beta, and an inhibiting agent of Smad3, a ligand trap (an antibody against a ligand, a decoy receptor), an antisense oligonucleotide, a TGF-beta receptor kinase inhibiting agent, a peptide aptamer, siRNA, shRNA, and the like (refer to Connolly E., et al., Int. J. Biol. Sci. 2012; 8(7): 964-978, FIG. 3, and the like).

Exemplary TGF-beta signal inhibiting agent that may be used in the present invention can include, without limitation, SB431542 (4-[4-(1,3-benzodioxol-5-yl)-5-(2-pyridinyl)]-1H-imidazol-2-yl]benzamide), BMP-7, anti-TGF-beta antibody, anti-TGF-beta receptor antibody, siRNA of TGF-beta, siRNA of TGF-beta receptor, antisense oligonucleotide of TGF-beta, 6,7-dimethoxy-2-((2E)-3-(1-methyl-2-phenyl-1H-pyrrolo[2,3-b]pyridin-3-yl-prop-2-enoyl))-1,2,3,4-tetrahydroisoquinolone, A83-01 (3-(6-methyl-2-pyridinyl)-N-phenyl-4-(4-quinolinyl)-1H-pyrazole-1-carbothioamide), Stemolecule™ TLK inhibitor (2-(3-(6-methylpyridin-2-yl)-1H-pyrazol-4-yl)-1,5-naphthyridine), Stemolecule™ BMP inhibitor LDN-193189 (6-(4-(piperidine-1-yl)ethoxy)phenyl)-3-(pyridin-4-yl)pyrazolo[1,5-a]pyrimidine), SD-208 (2-(5-chloro-2-fluorophenyl)-4-[(4-pyridinyl)amino]pteridine), LY364947 (4-[3-(2-pyridinyl)-1H-pyrazol-4-yl]-quinoline), pharmaceutically acceptable salts and a solvates thereof, and solvates of the pharmaceutically acceptable salts, and the like.

Other TGF-beta signal inhibiting agents include, without limitation, a monoclonal antibody and a polyclonal antibody to one or more isoforms of TGF-beta (U.S. Pat. No. 5,571,714; also see International Publication No. WO 97/13844 and International Publication No. WO 00/66631), TGF-beta receptor, a soluble form of such a receptor (e.g., soluble TGF-beta type III receptor), or an antibody directed to a TGF-beta receptor (U.S. Pat. Nos. 5,693,607, 6,001,969, 6,010,872, 6,086,867, 6,201,108; International Publication No. WO 98/48024; International Publication No. WO 95/10610; International Publication No. WO 93/09228; International Publication No. WO 92/00330), latent and associated peptide (International Publication No. WO 91/08291), large latent TGF-beta (International Publication No. WO 94/09812), fetuin (U.S. Pat. No. 5,821,227), other proteoglycan such as decorin and biglycan, fibromodulin, lumican, and endoglin and the like (International Publication No. WO 91/10727; U.S. Pat. Nos. 5,654,270, 5,705,609, 5,726,149; 5,824,655; International Publication No. WO 91/04748; U.S. Pat. Nos. 5,830,847, 6,015,693; International Publication No. WO 91/10727; International Publication No. WO 93/09800; and International Publication No. WO 94/10187), somatostatin (International Publication No. WO 98/08529), mannose-6-phosphoric acid or mannose-1-phosphoric acid (U.S. Pat. No. 5,520,926), prolactin (International Publication No. WO 97/40848), insulin-like growth factor II (International Publication No. WO 98/17304), IP-10 (International Publication No. WO 97/00691), Arg-Gly-Asp-containing peptide (Pfeffer, U.S. Pat. No. 5,958,411; International Publication No. WO 93/10808), plants, fungi and bacteria extracts (EP-A-813875; Japanese Laid-Open Publication No. 8-119984; and Matsunaga et al., U.S. Pat. No. 5,693,610), antisense oligonucleotide (U.S. Pat. Nos. 5,683,988; 5,772,995; 5,821,234, 5,869,462; and International Publication No. WO 94/25588), protein associated with TGF-beta signaling including Smad and MAD (EP-A-874046; International Publication No. WO 97/31020; International Publication No. WO 97/38729; International Publication No. WO 98/03663; International Publication No. WO 98/07735; International Publication No. WO 98/07849; International Publication No. WO 98/45467; International Publication No. WO 98/53068; International Publication No. WO 98/55512; International Publication No. WO 98/56913; International Publication No. WO 98/53830; International Publication No. WO 99/50296; U.S. Pat. Nos. 5,834,248; 5,807,708; and 5,948,639), Ski and Sno (Vogel, 1999, Science, 286:665; and Stroschein et al., 1999, Science, 286:771 to 774), one or more single-stranded oligonucleotide aptamers or an expression plasmid encoding them, suitable for inhibiting or interfering the binding of TGF-beta to a receptor of the same origin, and any mutant, fragment or derivative of a molecule identified above, which retains an ability to inhibit the activity of TGF-beta. The TGF-beta inhibiting agent may be a TGF-beta antagonist, and may be a human monoclonal antibody or a humanized monoclonal antibody (or F(ab)$_2$ fragment, Fv fragment, single chain antibody, and other forms or fragments of an antibody retaining the ability to bind to TGF-beta, a fragment thereof or the like), which blocks TGF-beta binding to the receptor. The TGF-beta receptor and a TGF-beta binding fragment, and in particular a soluble fragment, of a TGF-beta receptor are TGF-beta antagonists which are useful in the method according to the present invention. In a certain embodiment, an inhibiting agent preferable for TGF-beta functions is a soluble TGF-beta receptor, and in particular, a TGF-beta type II receptor (TGFBIIR) or a TGF-beta type III receptor (TGFBIIIR or betaglycan) including, for example, an extracellular domain of TGFBIIR or TGFBIIIR, preferably a recombinant soluble TGF-beta receptor (rsTGFBIIR or rsTGFBIIIR). The TGF-beta receptor and a TGF-beta binding fragment of the TGF-beta receptor, in particular a soluble fragment, are TGF-beta antagonists useful in the method according to the present invention. TGF-beta receptors and nucleic acids encoding them are sufficiently known in the art. A nucleic acid sequence encoding TGF-beta type 1 receptor is disclosed in GenBank accession number L15436 and U.S. Pat. No. 5,538,892 (Donahoe et al.). A nucleic acid sequence of a TGF-beta type 2 receptor is publicly available under GenBank accession number AW236001, AI35790, AI279872, AI074706, and AA808255. A nucleic acid sequence of a TGF-beta type 3 receptor is also publicly available under GenBank accession number NM003243, AI887852, AI817295, and AI681599.

In addition, still other TGF-beta signal inhibiting agents or antagonists and methods for producing them, are sufficiently known in the art, in addition to many of those that are currently under development. Any of effective TGF-beta antagonists may be useful in the method according to the present invention, and thus, specific TGF-beta signal inhibiting agents or antagonists used are not those with limited characteristics. Examples of such antagonists include monoclonal and polyclonal antibodies to TGF-beta of one or more isotypes (U.S. Pat. No. 5,571,714 and International Publication No. WO 97/13844), TGF-beta receptor, a fragment thereof, a derivative thereof, and an antibody to a TGF-beta receptor (U.S. Pat. Nos. 5,693,607, 6,008,011, 6,001,969 and 6,010,872, and International Publication No. WO 92/00330, International Publication No. WO 93/09228, International Publication No. WO 95/10610, and International Publication No. WO 98/48024); latency-associated peptide (latency associated peptide; International Publication No. WO 91/08291), large lacent TGF-beta (International Publication No. WO 94/09812), fetuin (U.S. Pat. No. 5,821,227), other proteoglycan such as decorin and biglycan, fibromodulin, lumican, endoglin, and the like (U.S. Pat. Nos. 5,583,103, 5,654,270, 5,705,609, 5,726,149, 5,824,655, 5,830,847, 6,015,693, and International Publication No. WO 91/04748, International Publication No. WO 91/10727, International Publication No. WO 93/09800 and International Publication No. WO 94/10187).

Further examples of such an antagonist include a host of other proteins associated with TGF-beta signaling, including somatostatin (International Publication No. WO 98/08529), mannose-6-phosphoric acid or mannose-1-phosphoric acid (U.S. Pat. No. 5,520,926), prolactin (International Publication No. WO 97/40848), insulin-like growth factor II (International Publication No. WO 98/17304), IP-10 (International Publication No. WO 97/00691), arginine (arg)-glycine (gly)-aspartic acid (asp)-containing peptide (U.S. Pat. No. 5,958,411 and International Publication No. WO 93/10808), plants, fungi and bacteria extracts (European Patent Application Publication No. 813875, Japanese Laid-Open Publication No. 8-119984 and U.S. Pat. No. 5,693,610), antisense oligonucleotide (U.S. Pat. Nos. 5,683,988, 5,772,995, 5,821,234 and 5,869,462, and International Publication No. WO 94/25588), and Smad and MAD (European Patent Application No. EP874046, International Publication No. WO 97/31020, International Publication No. WO 97/38729, International Publication No. WO 98/03663, International Publication No. WO 98/07735, International Publication No. WO 98/07849, International Publication No. WO 98/45467, International Publication No. WO 98/53068, International Publication No. WO 98/55512, International Publication No. WO 98/56913, International Publication No. WO 98/53830 and International Publication No. WO 99/50296, and U.S. Pat. Nos. 5,834,248, 5,807,708 and 5,948,639), and Ski and Sno (G. Vogel, Science, 286:665 (1999) and Stroschein et al., Science, 286:771-74(1999)), and any fragment and derivative of the above-mentioned molecule retaining the ability to inhibit the activity of TGF-beta.

The TGF-beta antagonists suitable for the use in the present invention also include a functional mutant, a mutant, a derivative, and an analogue of the aforementioned TGF-beta antagonist so long as their ability of inhibiting the amount or activity of TGF-beta is retained. The "mutant", "derivative", and "analogue" as used herein refers to a molecule having a form or structure similar to that of their parent compound, and retaining an ability to work as a TGF-beta antagonist. For example, any of the TGF-beta antagonists disclosed in the present specification may be crystallized, and useful analogues may be reasonably designed based on sites that have a role in forming (one or more) active sites. Instead, those skilled in the art can alter a functional group of known antagonists, or can screen such an altered molecule with regard to an increase of activity, half-life, bioavailability, or other desirable characteristics, without unnecessary experiments. When the TGF-beta antagonist is a polypeptide, a fragment and variant of the polypeptide may be produced to increase the ease of delivery, activity, half-life and the like (e.g., humanized antibodies or functional antibody fragments discussed above). In consideration of the technical level in the art for producing synthetic and recombinant polypeptides, such a variant may be achieved without unnecessary experiments. Those skilled in the art may also design a novel inhibiting agent based on knowledge on a crystal structure and/or active site of the TGF-beta inhibiting agent as described herein. A polypeptide inhibiting agent, such as a soluble TGF-beta receptor, may be effectively introduced through gene transfer. Accordingly, a certain embodiment for the method according to the present invention includes use of a vector suitable for expression of a TGF-beta receptor or a binding partner, preferably a soluble receptor or a soluble binding partner. In a preferable embodiment, administration of a soluble TGF-beta antagonist can be achieved by gene transfer which uses a vector comprising a cDNA encoding a soluble antagonist or a cDNA encoding an extracellular domain of a TGF-beta type II receptor (rsTGFBIIR) or a TGF-beta type III receptor (rsTGFBIIIR). This vector causes an in situ expression of a soluble TGF-beta antagonist in a cell which is transfected using the vector, inhibits the activity of TGF-beta, and suppresses TGF-beta-mediated fibrogenesis. Any suitable vector can be used. Preferable vectors include an adenovirus vector, a lentivirus vector, an Epstein-Barr virus (EBV) vector, an adeno-associated virus (AAV) vector, and a retrovirus vector, developed for the purpose of gene transfer. Other non-vector methods for gene transfer may also be used, such as lipid/DNA complex, protein/DNA conjugate and naked DNA transfer methods. Further suitable TGF-beta antagonists developed for delivery via adenovirus gene transfer include, without limitation, a chimeric cDNA encoding an extracellular domain of a TGF-beta type II receptor, fused to an Ig Fc domain (Isaka et al., 1999, Kidney Int., 55:pp. 465 to 475), an adenovirus gene transfer vector of a dominant negative mutant of a TGF-beta type II receptor (Zhao et al., 1998, Mech. Dev., 72:pp. 89 to 100), and an adenovirus gene transfer vector of decorin, which is a TGF-beta binding proteoglycan (Zhao et al., 1999, Am. J. Physiol., 277: pp. L412 to L422). Adenovirus-mediated gene transfer has extremely high efficiency compared to other gene delivery manners.

The TGF-beta receptor and a TGF-beta binding fragment, a soluble fragment and the like of the TGF-beta receptor are TGF-beta antagonists useful in the present invention. The TGF-beta receptors and nucleic acids encoding them are sufficiently known in the art. The nucleic acid sequence encoding the TGF-beta type 1 receptor is disclosed in GenBank, accession number L15436 and U.S. Pat. No. 5,538,892 by Donahoe et al. A nucleic acid sequence of the TGF-beta type 2 receptor is also publicly available under GenBank accession number AW236001; AI35790; AI279872; AI074706; and AA808255. A nucleic acid sequence of the TGF-beta type 3 receptor is also publicly available under GenBank accession number NM003243; AI887852; AI817295; and AI681599. In one exemplary embodiment, the TGF-beta antagonist is an antibody which blocks TGF-beta binding to a receptor thereof, or to fragments thereof such as a F(ab)$_2$ fragment, a Fv fragment, a single-stranded antibody, and other "antibody" types retaining the ability to bind to TGF-beta. The antibody thereof may be chimerized or humanized. Herein, the chimerized antibody includes a constant region of a human antibody, and a variable region of non-human antibodies such as a murine antibody. The humanized antibody includes a constant region and a framework variable region (i.e., variable regions other than hypervariable regions) of a human antibody, and a hypervariable region of non-human antibodies such as a murine antibody. As a matter of course, the antibody may be any other types of antibody derivatives, such as human antibodies selected from a phage display system or produced from a XenoMouse.

Findings related to Smad are increasing. TGF-beta signal transduction pathway is initiated when this molecule binds to a heterodimer cell surface complex consisting of a serine/threonine kinase receptor of type I (TbRI) and type II (TbRII) and induces this heterodimer cell surface complex. Then, the heterodimer receptor transmits said signal through phosphorylation of a target Smad protein in the downstream. As described above, there are three functional classes for the Smad protein, and they are, for example, Smad (R-Smad) restricted by a receptor such as Smad2 and Smad3, a co-mediator (Co-Smad) which is also referred to as Smad4, and an inhibitory Smad (I-Smad). Followed by the phosphorylation by the heterodimer receptor complex, this R-Smad forms a complex with this Co-Smad, moves to said nucleus, and working together with other respective proteins, they regulate transcription of the target gene (Derynck, R., et al. (1998) Cell 95: 737-740); Massague, J. and Wotton, D. (2000) EMBO J. 19:1745). A nucleotide sequence and an amino acid sequence of human Smad3 are disclosed in, for example, GenBank Accession No. gi:42476202. A nucleotide sequence and an amino acid sequence of murine Smad3 is disclosed in, for example, GenBank Accession No. gi: 31543221. As described above, TGF-beta stimulation provides phosphorylation and activation of Smad2 and Smad3, which form a complex with Smad4 (also referred to as "common Smad" or "co-Smad"), and the complex is accumulated with a nucleus to regulate the transcription of the target gene. Accordingly, the TGF-beta signal inhibition may also be achieved by inhibition of Smad2, 3 or co-Smad (Smad4). The R-Smad is localized in a cytoplasm, and forms a complex with a co-Smad through ligand-induced phosphorylation by a TGF-beta receptor to move to a nucleus, in which they regulate gene expression associated with a chromatin and a cooperative transcription factor. Thus, TGF-beta signal inhibition can also be achieved by inhibiting R-Smad either directly or indirectly. Smad6 and Smad7 are inhibitory Smad (I-Smad), and that is, they are transcriptionally induced by TGF-beta to function as an inhibiting agent of TGF-beta signaling (Feng et al., (2005) Annu. Rev. Cell. Dev. Biol. 21: 659). Smad6/7 prevents receptor-mediated activation of R-Smad, thereby exerting their inhibitory effect. They are associated with a type I receptor, which competitively inhibits mobilization and phosphorylation of R-Smad. Smad6 and Smad7 are known to replenish E3 ubiquitin ligase, which causes ubiquitination and degradation of Smad6/7 interactive protein. Thus, Smad6 and 7 can function as a TGF-beta signal inhibiting agent in the present invention.

The inhibiting agents of Smad3 that may be used in the present invention can include, without limitation, antisense nucleotide, siRNA, antibody and the like, and in addition, 6,7-dimethoxy-2-((2E)-3-(1-methyl-2-phenyl-1H-pyrrolo [2,3-b]pyridin-3-yl-prop-2-eno yl))-1,2,3,4-tetrahydroisoquinolone, and the like commercially available from Calbiochem, as a low-molecular compound.

As used herein, "substance (e.g., nucleic acid) for suppressing expression (of TGF-beta or the like)" is not particularly limited so long as such a substance is a substance which suppresses transcription of mRNA of a target gene, a substance which degrades a transcribed mRNA (e.g., nucleic acid), or a substance (e.g., nucleic acid) which suppresses translation of protein from mRNA. As to the substances, exemplified are siRNA, antisense oligonucleotide, and ribozyme as well as nucleic acids of expression vectors. Among them, siRNA and an expression vector thereof are preferable, and siRNA is particularly preferable. "Substance which suppresses expression of a gene" includes, in addition to those described above, protein, peptide, and other small molecules. Note that a target gene in the present invention means any gene that is associated with a TGF-beta signal transduction pathway.

As to a method for inhibiting the expression of a specific endogenous gene, such as TGF-beta, that is targeted in the present invention, a method utilizing an antisense technique is well known to those skilled in the art. As to actions for an antisense nucleic acid to inhibit the expression of a target gene, there are a plurality of factors as follows. Specifically, such factors are: inhibition of transcript initiation due to triplex formation; inhibition of transcription due to hybrid formation with a site where an open loop structure is locally formed due to RNA polymerase; inhibition of transcription due to hybrid formation with an RNA whose synthesis is in progress; splicing inhibition due to hybrid formation at a junction of intron and exon; splicing inhibition due to hybrid formation with spliceosome forming site; transfer inhibition from a nucleus to cytoplasm due to hybrid formation with mRNA; splicing inhibition due to hybrid formation with a capping site or a poly (A) addition site; inhibition of translation initiation due to hybrid formation with a translation initiation factor binding site; translational inhibition due to hybrid formation with a ribosome binding site near an initiation codon; elongation inhibition of a peptide chain due to hybrid formation with a polysome binding site or a translation region of mRNA; and gene expression inhibition due to hybrid formation with a interaction site of a nucleic acid and a protein, and the like. As such, an antisense nucleic acid inhibits a variety of processes, such as transcription, splicing or translation, to inhibit the expression of a target gene (Hirashima and Inoue, Shinsei Kagaku Jikken Kouza [New Chemical Experiment Course] 2, Nucleic Acid, IV Idenshi no Fukusei to Hatsugen [Duplication and Expression of Gene], Edited by the Japanese Biochemical Society, Tokyo Kagaku Dozin, 1993, 319-347).

The antisense nucleic acid used in the present invention may inhibit the expression and/or function of a gene (nucleic acid) encoding a member or the like of a signal transduction pathway of the above-mentioned TGF-beta by any of the above-mentioned actions. In one embodiment, it is considered to be effective for the translation inhibition of a gene when an antisense sequence complementary to a non-translation region near 5' terminal of mRNA of a gene encoding the above-mentioned TGF-beta or the like is designed. In addition, it is possible to use a sequence complementary to a coding region or a 3' non-translation region. As such, the translation region of a gene encoding the above-mentioned TGF-beta or the like as well as a nucleic acid including an antisense sequence of a sequence of a non-translation region are included in the antisense nucleic acid that are used in the present invention. The antisense nucleic acid used is connected to a downstream of an appropriate promoter, and is preferably connected to a sequence including a transcription termination signal on the side closer to 3'. A nucleic acid prepared in such a manner can be transformed into a desired animal (cell) using a publicly known method. While the sequence of the antisense nucleic acid is preferably a sequence complementary to a gene, or a part thereof, encoding TGF-beta or the like of an animal (cell) to be transformed, it does not have to be completely complementary so long as the sequence can effectively suppress the expression of genes. The transcribed RNA preferably has 90% or more, and most preferably 95% or more, complementarity to a transcription product of a target gene. In order to effectively inhibit the expression of a target gene using an antisense nucleic acid, the length of the antisense nucleic acid is preferably at least 12 bases or more but less than 25 bases long. However, the antisense nucleic acid according to the present invention is not necessarily limited to this length, and the antisense nucleic acid may be, for example, 11 bases or less, 100 bases or more, or 500 bases or more. While the antisense nucleic acid may be composed of DNA only, it may also include nucleic acids other than DNA, such as locked nucleic acid (LNA). In one embodiment, the antisense nucleic acid used in the present invention may be a LNA-containing antisense nucleic acid including LNA at the 5' terminal, and LNA at the 3' terminal. Furthermore, in an embodiment where an antisense nucleic acid is used in the present invention, an antisense sequence can be designed based on a nucleic acid sequence, such as TGF-beta, using a method described in Hirashima and Inoue, Shinsei Kagaku Jikken Kouza [New Chemical Experiment Course] 2, Nucleic Acid, IV Idenshi no Fukusei to Hatsugen [Duplication and Expression of Gene], Edited by the Japanese Biochemical Society, Tokyo Kagaku Dozin, 1993, 319-347, for example.

The inhibition of expression of TGF-beta or the like can also be performed by using ribozyme, or DNA encoding ribozyme. The ribozyme refers to a RNA molecule having catalytic activity. There are various types of ribozymes having various types of activities, and researches focusing on especially a ribozyme as an enzyme for cleaving RNA has made it possible to design a ribozyme for cleaving RNA in a site-specific manner. While ribozymes include those with 400 nucleotides or more in size, such as group I intron type and M1 RNA included in RNase P, there are also such ribozymes having an activity domain of as many as 40 nucleotides, such as those referred to as hammer head type and hairpin type (Makoto Koizumi and Eiko Ohtsuka, Tanpakushitu Kakusan Kouso [Protein Nucleic Acid Enzyme], 1990, 35, 2191).

For example, the self-cleavage domain of the hammer head type ribozyme cleaves the side closer to 3' of C15 in a sequence referred to as G13U14C15, and the base-pair formation of U14 and A9 is considered to be important for the activity thereof; and it is indicated that cleavage can be made by A15 or U15, instead of C15 (Koizumi, M. et al., FEBS Lett, 1988, 228, 228). If a ribozyme is designed in which a substance binding site is complementary to a RNA sequence near a target site, a restriction-enzymic RNA cleavage ribozyme can be created which recognizes a sequence such as UC, UU or UA in a target RNA (Koizumi, M. et al., FEBS Lett, 1988, 239, 285., Makoto Koizumi and Eiko Ohtsuka, Tanpakushitu Kakusan Kouso [Protein Nucleic Acid Enzyme], 1990, 35, 2191., Koizumi, M. et al., Nucl. Acids Res., 1989, 17, 7059).

In addition, hairpin type ribozyme are also useful for the purpose of the present invention. Such a ribozyme is found in, for example, a negative strand of a satellite RNA of tobacco ringspot virus (Buzayan, J M., Nature, 1986, 323, 349). It is indicated that a target-specific RNA cleavage ribozyme can be created from hairpin type ribozyme (Kikuchi, Y. & Sasaki, N., Nucl. Acids Res, 1991, 19, 6751., Kikuchi, Yo, Kagaku to Seibutu [*Chemistry and Living Organism*], 1992, 30,112). As such, a transcription product of a gene encoding TGF-beta or the like is specifically cleaved using ribozyme, so that the expression of the gene can be inhibited.

Suppression of expression of an endogenous gene of TGF-beta or the like can also be performed by RNA interference (hereinafter, abbreviated as "RNAi") using a double-stranded RNA having a sequence identical or similar to a target gene sequence. With regard to the RNAi, when double-stranded RNA (dsRNA) is taken directly into a cell, expression of a gene having a sequence homologous to the dsRNA is suppressed, which is a method that is currently attracting attention. In mammalian cells, a short strand dsRNA (siRNA) is used so that RNAi can be induced. In comparison with knockout mice, RNAi has many advantages, such as high stability of an effect, easy experimentation, and inexpensive cost. The siRNA will be described in detail in a different part of the present specification.

As used herein, "siRNA" refers to an RNA molecule having a double-stranded RNA moiety consisting of 15 to 40 bases, and the siRNA has a function of cleaving mRNA of a target gene having a sequence complementary to an antisense strand of said siRNA and suppressing the expression of the target gene. More specifically, the siRNA according to the present invention is an RNA including a double-stranded RNA moiety consisting of a sense RNA chain consisting of a sequence homologous to a contiguous RNA sequence in mRNA of TGF-beta or the like, and an antisense RNA chain consisting of a sequence complementary to the sense RNA sequence. The manufacturing and designing of the siRNA and a mutant siRNA to be described below are within the scope of the ability of those skilled in the art. The concept of selecting any contiguous RNA region of mRNA, which is a transcription product of a sequence of TGF-beta or the like, and creating a double-stranded RNA corresponding to the region is merely a matter that those skilled in the art can perform within the normal creative ability of them. Furthermore, the concept of selecting a siRNA sequence with a more powerful RNAi effect from an mRNA sequence, which is a transcription product of the subject sequence, can be appropriately performed by those skilled in the art using a publicly known method. Furthermore, if one of the strands is identified, it is easy for those skilled in the art to determine a base sequence of the other strand (complementary strand). Those skilled in the art can appropriately create siRNA using a commercially available nucleic acid synthesizing machine. In addition, synthesis entrustment service can be generally used for desired RNA synthesis.

The length of the double-stranded RNA moiety is, as a base, 15 to 40 bases, preferably 15 to 30 bases, more preferably 15 to 25 bases, still more preferably 18 to 23 bases, and most preferably 19 to 21 bases. It is understood that the upper and lower limits thereof are not limited to the specified ones, but the limits can be any combinations of the listed ones. As to a terminal structure of a sense strand or antisense strand of siRNA, there is no particular limitation, and it can be appropriately selected depending on the purpose. For example, the terminal structure may be the one having a flush terminal or the one having protruding terminal (overhang), and the type with protruded 3' terminal is preferable. A siRNA having an overhang consisting of several bases, preferably 1 to 3 bases, and still preferably 2 bases, at the 3' terminal of the sense RNA strand and antisense RNA strand often has a great effect of inhibiting the expression of a target gene, which is preferable. The type of the bases of overhang is not particularly restricted, and the type can be either a base constituting an RNA or a base constituting a DNA. Preferable overhang sequences can include dTdT (2 bp deoxy T) at the 3' terminal, and the like. For example, preferable siRNAs include, without limitation, those in which dTdT (2 bp deoxy T) is added to 3' terminal of the sense and antisense strands of all the siRNA.

Furthermore, it is also possible to use a siRNA in which one to several nucleotides are deleted, substituted, inserted and/or added in either or both of the sense strand and antisense strand of the above-mentioned siRNA. In this regard, the concept of one to several bases is not particularly limited, but it is preferably 1 to 4 bases, still preferably 1 to 3 bases, most preferably 1 to 2 bases. Specific examples of the subject mutation include, without limitation, those in which the number of bases at the 3' overhang moiety is from 0 to 3, those in which the base sequence of the 3'-overhang moiety is changed to another base sequence, those in which the length of the above-mentioned sense RNA strand and antisense RNA strand is different by 1 to 3 bases due to the insertion, addition or deletion of bases, those in which the base in a sense strand and/or antisense strand is substituted with another base, and the like. However, it is necessary for the sense strand and the antisense strand to be able to hybridize in these mutant siRNAs, and it is necessary for these mutant siRNAs to have an ability to inhibit gene expression equivalent to siRNAs that do not have mutation.

Furthermore, the siRNA may be a siRNA (Short Hairpin RNA; shRNA) in which one of the terminals has a molecule of a closed structure, such as a hairpin structure. The shRNA is a sense strand RNA of a specific sequence of a target gene, an antisense strand RNA consisting of a sequence complementary to the sense strand sequence, and a RNA including a linker sequence for connecting the both strands thereof, wherein the sense strand moiety and the antisense strand moiety hybridize to form a double-stranded RNA moiety.

The siRNA desirably does not exhibit a so-called off-target effect when clinically used. The off-target effect refers to an effect for suppressing the expression of another gene with partially homology to the siRNA used, other than the target gene. In order to avoid the off-target effect, it is possible to confirm that a candidate siRNA does not have cross reactivity using DNA microarray or the like in advance. Furthermore, it is possible to avoid the off-target effect by confirming as to whether there is a gene including a moiety having high homology with a sequence of a candidate siRNA, other than a target gene, using publicly known database provided by NCBI (National Center for Biotechnology Information) or the like.

In order to create the siRNA according to the present invention, a publicly known method, such as a method by chemical synthesis and a method using a gene recombination technique, can be appropriately used. With a method by synthesis, a double-stranded RNA can be synthesized based on sequence information, using an ordinary method. In addition, in a method using a gene recombination technique, it is also possible to create such a siRNA by constructing an expression vector encoding a sense strand sequence and an antisense strand sequence and introducing the vector into a host cell, and then obtaining a sense strand RNA and antisense strand RNA, each of which is produced by transcription. Furthermore, it is possible to create a desired double-stranded RNA by expressing a shRNA, which includes a sense strand of a specific sequence of a target gene, an antisense strand consisting of a sequence complementary to the sense strand sequence, and a linker sequence for connecting the both strands, and which forms a hairpin structure.

With regard to the siRNA, all or part of the nucleic acids constituting the siRNA may be a natural nucleic acid or a modified nucleic acid so long as such a nucleic acid has an activity to suppress the expression of a target gene.

The siRNA according to the present invention does not necessarily have to be a pair of double-stranded RNAs to a target sequence, and it may be a mixture of a plurality (the "plurality" is not particularly limited, but preferably refers to a small number of about 2 to 5) of double-stranded RNAs to a region which includes a target sequence. In this regard, those skilled in the art can appropriately create siRNA, as a nucleic acid mixture corresponding to a target sequence, using a commercially available nucleic acid synthesizing machine and DICER enzyme; and as to synthesis of a desired RNA, synthesis entrustment service can be generally used. Note that the siRNA according to the present invention includes a so-called "cocktail siRNA". Furthermore, note that the siRNA according to the present invention is such that not all the nucleotides have to be a ribonucleotide (RNA). Specifically, in the present invention, one or plurality of ribonucleotides constituting a siRNA may be a corresponding deoxyribonucleotide. The term "corresponding" refers to being the same base type (adenine, guanine, cytosine, thymine (uracil)) although the structure of the sugar portion is different. For example, a deoxyribonucleotide corresponding to a ribonucleotide having adenine refers to a deoxyribonucleotide having adenine.

Furthermore, a DNA (vector) which may express the above-mentioned RNA according to the present invention is also included in a preferred embodiment of a nucleic acid which may suppress expression of TGF-beta or the like. For example, the DNA (vector) which may express the above-mentioned double-stranded RNA according to the present invention is such a DNA having a structure in which DNA encoding one of the strands of the double-stranded RNA and a DNA encoding the other of the strands of the double-stranded RNA are connected to a promoter so that each of the DNAs is capable of being expressed. The above-mentioned DNA according to the present invention can be appropriately created by those skilled in the art using a general genetic engineering technique. More specifically, the expression vector according to the present invention can be created by appropriately inserting the DNA encoding RNA according to the present invention, into a variety of publicly known expression vectors.

In the present invention, a modified nucleic acid may be used for the nucleic acid for suppressing the expression of a target gene. The modified nucleic acid means a nucleic acid in which modification is provided at a nucleoside (base moiety, sugar moiety) and/or an inter-nucleoside binding site, and that has a structure different from that of a natural nucleic acid. "Modified nucleoside", which constitutes a modified nucleic acid, includes, for example, abasic nucleoside; arabinonucleoside, 2'-deoxyuridine, alpha-deoxyribonucleoside, beta-L-deoxyribonucleoside, nucleoside having other sugar modification; peptide nucleic acid (PNA), phosphate group-binding peptide nucleic acid (PHONA), locked nucleic acid (LNA), morpholino nucleic acid and the like. The above-mentioned nucleoside having sugar modification includes nucleosides having a substituted pentose, such as 2'-O-methylribose, 2'-deoxy-2'-fluororibose, 3'-O-methylribose, and the like; 1',2'-deoxyribose; arabinose; a substituted arabinose sugar; and a hexose, and sugar modification of an alpha-anomer. These nucleosides may be a modified base in which the base moiety is modified. Such modified bases include, for example, pyrimidine, such as 5-hydroxycytosine, 5-fluorouracil, 4-thiouracil, and the like; purine, such as 6-methyladenine, 6-thioguanosine, and the like; and other heterocyclic bases.

"Modified inter-nucleoside binding", which constitutes a modified nucleic acid, includes non-natural inter-nucleoside binding, such as alkyl linker, glyceryl linker, amino linker, poly(ethylene glycol) binding, inter-methyl phosphonate nucleoside binding; methylphosphonothioate, phosphotriester, phosphothiotriester, phosphorothioate, phosphorodithioate, triester prodrug, sulfone, sulfonamide, sulfamate, form acetal, N-methylhydroxylamine, carbonate, carbamate, morpholino, boranophosphonate, phosphoramidate and the like.

The nucleic acid sequence included in the double-stranded siRNA according to the present invention can include a siRNA directed to a member of TGF-beta or other TGF-beta signaling members, and the like.

It is also possible to introduce the nucleic acid or agent according to the present invention into phospholipid endoplasmic reticulums, such as liposome and the like, and administer the endoplasmic reticulum. An endoplasmic reticulum in which a siRNA or shRNA is retained can be introduced into a predetermined cell using a lipofection method. Then, the obtained cell is systemically-administered, for example intravenously, intra-arterially, or the like. The endoplasmic reticulum can also be locally administered to a required site in an eye or the like. While the siRNA exhibits an extremely excellent specific post-transcription suppressing effect in vitro, it is quickly degraded in vivo due to nuclease activity in blood serum. Thus, the duration is limited, and because of this, there has been a need for development for a better and more effective delivery system. As to one example, Ochiya, T et al., Nature Med., 5:707-710, 1999, Curr. Gene Ther., 1: 31-52, 2001 reports as follows: a biocompatible material, atelocollagen, is mixed with a nucleic acid to form a complex, which has an action for protecting a nucleic acid from a degrading enzyme in a living organism and which is a carrier that is extremely suitable as a carrier for siRNA. While such a form can be used, the method for introducing a nucleic acid or medicament according to the present invention is not limited to this method. As such, due to quick degradation by the action of the nucleic acid degrading enzyme in blood serum in a living organism, it becomes possible to achieve long-time continuation of the effect. For example, Takeshita F. PNAS. (2003) 102(34) 12177-82, Minakuchi Y Nucleic Acids Research (2004) 32 (13) e109 reports as follows: atelocollagen derived from bovine skin forms a complex with a nucleic acid, which has an action for protecting a nucleic acid from degrading enzyme in a living organism and which is extremely suitable as a carrier of siRNA. Such a technique can be used.

As used herein, an "agent" is used in a broad sense, and may be any substance or other elements (e.g., energy such as light, radiation, heat, and electricity) as long as the intended objective can be attained. Examples of such a substance include, but are not limited to, proteins, polypeptides, oligopeptides, peptides, polynucleotides, oligonucleotides, nucleotides, nucleic acids (e.g., including DNA such as cDNA and genomic DNA, and RNA such as mRNA), polysaccharides, oligosaccharides, fats, organic small molecules (e.g., hormones, ligands, information transmitting substances, organic small molecules, molecules synthesized by combinatorial chemistry, small molecules which can be utilized as a pharmaceutical product (e.g., a low molecular weight ligand) and the like), and composite molecule thereof. Representative examples of an agent specific to a polynucleotide include, but are not limited to, a polynucleotide having complementarity with certain sequence homology (e.g., 70% or more sequence identity) relative to the sequence of the polynucleotide, a polypeptide such as a transcription factor binding to a promoter region. Representative examples of an agent specific to a polypeptide include, but are not limited to, an antibody specifically directed to the polypeptide or a derivative or an analog thereof (e.g., single-stranded antibody), a specific ligand or receptor when the polypeptide is a receptor or a ligand, and a substrate when the polypeptide is an enzyme.

As used herein, "a disease, disorder, or condition associated with extracellular matrix (ECM) abnormality in a corneal endothelium" refers to those diseases, disorders, or conditions associated with extracellular matrix (ECM) abnormality of diseases, disorders, or conditions in a corneal endothelium. As such, examples can include disorders related to Fuchs' endothelial corneal dystrophy, pterygium, allergic diseases, keratitis, corneal ulcer, and the like.

As used herein, "a disorder related to Fuchs' endothelial corneal dystrophy" refers to any disorders related to Fuchs' endothelial corneal dystrophy. Of these, disorders associated with extracellular matrix (ECM) abnormality are particularly targeted by the present invention, but it is not limited to the disorders. Examples of disorders related to Fuchs' endothelial corneal dystrophy that are associated with such extracellular matrix (ECM) abnormality include, but not limited to, photophobia, blurred vision, vision disorder, eye pain, lacrimation, hyperemia, pain, bullous keratopathy, ophthalmic unpleasantness, a decrease in contrast, glare, edema in corneal stroma, bullous keratopathy, corneal opacity, and the like.

(General Techniques)

Molecular biological methods, biochemical methods, and microbiological methods used herein are well known and commonly used in the art, which are described in, for example, Sambrook J. et al., (1989). Molecular Cloning: A Laboratory Manual, Cold Spring Harbor and the 3rd Ed. (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al., (1999). PCR Applications: Protocols for Functional Genomics, Academic Press, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press, Experimental Medicine, separate volume, "Gene Introduction & Expression Analysis Experimental Method" Yodosha Co., Ltd., 1997, and the like. With regard to corneal endothelial cells, the report from Nancy Joyce et al., {Joyce, 2004 #161} {Joyce, 2003 #7} is well known, while researches are currently conducted for effective culturing methods by conducting transformation in a fibroblastic manner through long-term culturing and subculturing as described above. With regard to these, the relevant portion thereof (can be the entire document) is incorporated herein by reference.

DESCRIPTION OF PREFERRED EMBODIMENT

Hereinafter, preferred embodiments will be described, but it should be understood that the embodiments are exemplification of the present invention and the scope of the present invention is not limited to such preferred embodiments. It should also be understood that those skilled in the art can easily perform alteration, change, and the like within the scope of the present invention with reference to the following preferable Examples.

(A Medicament for Treating or Preventing a Disease, Disorder, or Condition Associated with Extracellular Matrix (ECM) Abnormality in a Corneal Endothelium, Comprising a TGF-Beta Signal Inhibiting Agent)

In one aspect, the present invention provides medicaments for treating or preventing a disease, disorder, or condition associated with extracellular matrix (ECM) abnormality in a corneal endothelium, the medicaments comprise a TGF-beta signal inhibiting agent. In the present invention, it was found that a disease, disorder, or condition associated with ECM in a corneal endothelium, unexpectedly ECM abnormality, could be reduced or made disappear by administering a TGF-beta signal inhibiting agent. Accordingly, it can be recognized that a use of such a TGF-beta signal inhibiting agent for the treatment or prevention of a disease, disorder, or condition associated with extracellular matrix (ECM) abnormality in a corneal endothelium could not be expected from previous knowledge.

In a preferable embodiment, a disease, disorder, or condition intended by the present invention is a disorder related to Fuchs' endothelial corneal dystrophy. For Fuchs' endothelial corneal dystrophy, currently, there is no radical therapeutic method or technique, and therapy against Fuchs' endothelial corneal dystrophy had to rely on keratoplasty. Since the present invention can treat extracellular matrix (ECM) abnormality that causes one important abnormality or disorder in Fuchs' endothelial corneal dystrophy, it is understood to be useful in treatment or prevention of Fuchs' endothelial corneal dystrophy.

In one certain embodiment, diseases, disorders, or conditions intended by the present invention include photophobia, blurred vision, vision disorder, eye pain, lacrimation, hyperemia, pain, bullous keratopathy, ophthalmic unpleasantness, a decrease in contrast, glare, edema in corneal stroma, and corneal opacity in Fuchs' endothelial corneal dystrophy.

The subject of the administration (transplantation) of the medicament or method according to the present invention includes mammals (e.g., humans, mice, rats, hamsters, rabbits, cats, dogs, cows, horses, sheep, monkeys, and the like), and the subject is preferably primates, and particularly preferably humans. Therapy for corneal endothelium in primates had not achieved sufficient results before, and from that point of view, the present invention provides an innovative therapeutic method and medicament.

TGF-beta signal transduction pathways are broadly classified into the Smad2/3 system through ALK4, 5, or 7 and the Smad1/5/8 system through ALK1, 2, 3, or 6. Both of them are well known to be related to fibrosis (J. Massagu'e, Annu. Rev. Biochem. 1998.67:753-91; Vilar J M G, Jansen R, Sander C (2006) PLoS Comput Biol 2(1):e3; Leask, A., Abraham, D. J. FASEB J. 18, 816-827 (2004); Coert Margadant & Arnoud Sonnenberg EMBO reports (2010) 11, 97-105; Joel Rosenbloom et al., Ann Intern Med. 2010; 152:159-166). It is also known that BMP-7 can suppress a TGF-beta signal to suppress fibrosis (other than the above-described literatures, Ralf Weiskirchen, et al., Frontiers in Bioscience 14, 4992-5012, Jun. 1, 2009; Elisabeth M Zeisberg et al., Nature Medicine 13, 952-961 (2007); Michael Zeisberg et al., Nature Medicine 9, 964-968 (2003)). However, these literatures describe involvement with TGF-beta with regard to luetic interstitial keratitis, which is a very special disease, or such a state as to accompany a membrane-shaped tissue actually consisting of an extracellular substrate, such as collagen and the like, by a severe disorder made artificially. However, it is difficult to expect a therapeutic effect from this description. In addition, those literatures show that fibrosis at the time of a corneal severe disorder is caused by IL-1beta, or by activation of p38 MAPK halfway, while those show, using a rabbit, that fibrosis seen when severe inflammation in a living body occurs due to excess freezing trauma in a rabbit accompanies activation of p38 MAPK, and an inhibiting agent can partly suppress fibrosis. These pieces of knowledge show that activation of p38 MAPK is accompanied in such a condition that very strong inflammation occurs in a living body and a membrane-shaped tissue consisting of an extracellular substrate is accompanied. Those do not mention that a TGF-beta signal inhibiting agent is effective to treat or prevent a disease, disorder, or condition associated with extracellular matrix (ECM) abnormality in a corneal endothelium of Fuchs' endothelial corneal dystrophy and the like. Those suggest nothing about maintenance of a normal condition. As described above, it was previously believed difficult to culture a corneal endothelial cell with keeping the normal functions. In the previous reports, finally, a disease, disorder, or condition associated with extracellular matrix (ECM) abnormality in a corneal endothelium of Fuchs' endothelial corneal dystrophy and the like could not be treated or prevented, let alone it was not believed possible to treat or prevent a disease, disorder, or condition associated with extracellular matrix (ECM) abnormality in a corneal endothelium of Fuchs' endothelial corneal dystrophy and the like by suppressing TGF-beta signal transduction pathways.

The TGF-beta signal inhibiting agent used in the present invention may be any agent as long as the agent can inhibit the signal pathway of TGF-beta. In addition, the TGF-beta signal transduction pathway to be inhibited may be associated with a factor associated with any signal, as long as such a signal transduction pathway ultimately exerts an effect similar (opposite in a case of an inhibiting agent, an antagonist, or the like) to the signal transduction pathway of TGF-beta, like BMP-7, in addition to signal transduction pathways with which TGF-beta and a TGF-beta receptor are directly associated, as is well known.

In the present invention, it is possible to include a TGF-beta signal inhibiting agent alone, and it is also possible to include several types thereof in combination with each other as needed.

In one embodiment, the TGF-beta signal inhibiting agent includes at least one of an antagonist of TGF-beta, an antagonist of a receptor of TGF-beta, or an inhibiting agent of Smad3, ingredients illustrated in other parts of the present specification, a pharmaceutically acceptable salt or a solvate thereof, or a solvate of the pharmaceutically acceptable salt. As for the antagonist of TGF-beta, the antagonist of a receptor of TGF-beta, and the inhibiting agent of Smad3, any one of them described in other parts of the present specification can be used.

In one embodiment, TGF-beta signal inhibiting agents that may be used in the present invention include at least one of SB431542 (4-[4-(1,3-benzodioxol-5-yl)-5-(2-pyridinyl)-1H-imidazol-2-yl]benzamide), BMP-7, anti-TGF-beta antibody, anti-TGF-beta receptor antibody, siRNA of TGF-beta, siRNA of a TGF-beta receptor, an antisense oligonucleotide of TGF-beta, 6,7-dimethoxy-2-((2E)-3-(1-methyl-2-phenyl-1H-pyrrolo[2,3-b]pyridin-3-yl-prop-2-enoyl))-1,2,3,4-tetra-hydroisoquinolone, A83-01 (3-(6-methyl-2-pyridinyl)-N-phenyl-4-(4-quinolinyl)-1H-pyrazole-1-carbothioamide), Stemolecule™ TLK inhibitor (2-(3-(6-methylpyridin-2-yl)-1H-pyrazol-4-yl)-1,5-naphthyridine), Stemolecule™ BMP inhibitor LDN-193189 (6-(4-(piperidin-1-yl)ethoxy)phenyl)-3-(pyridin-4-yl)pyrazolo[1,5-a]pyrimidine), SD-208 (2-(5-chloro-2-fluorophenyl)-4-[(4-pyridinyl)amino]pteridine), LY364947 (4-[3-(2-pyridinyl)-1H-pyrazol-4-yl]-quinoline), components illustrated in other parts of the present specification, pharmaceutically acceptable salts or solvates thereof, or solvates of the pharmaceutically acceptable salts. It should be noted that the above-mentioned antibodies may be, but not limited to, neutralizing antibodies. Without wishing to be bound by any theory, an effect of treating or preventing a disease, disorder, or condition associated with extracellular matrix (ECM) abnormality in a corneal endothelium of Fuchs' endothelial corneal dystrophy and the like is observed for both of SB431542 that attains an effect through Smad2/3 (related to ALK4, 5, and 7), and BMP-7 that attains an effect through Smad1/5/8 (related to ALK1, 2, 3, and 6). Accordingly, it is understood that even if they are TGF-beta signal inhibiting agents for either of these pathways, the effect of the present invention can be achieved.

In a preferable embodiment, TGF-beta signal inhibiting agents used in the present invention include SB431542 (4-[4-(1, 3-benzodioxol-5-yl)2-pyridinyl)-1H-imidazol-2-yl]benzamide). The reason is that improvement of a disease, disorder, or condition associated with extracellular matrix (ECM) abnormality in a corneal endothelium of Fuchs' endothelial corneal dystrophy and the like was exhibited. In a preferred embodiment, SB431542 is included to be present at a concentration of about 0.1 µM to about 10 µM in use, preferably included to be present at a concentration of about 1 µM to about 10 µM in use, and further preferably included to be present at a concentration of about 1 µM in use.

The concentration of the TGF-beta signal inhibiting agent used in the present invention is normally about 0.1 to 100 µmol/l, preferably about 0.1 to 30 mol/l, and more preferably about 1 µmol/l; when several types thereof are used, the concentration may be changed appropriately, and examples of other concentration ranges are normally about 0.001 to 100 µmol/l, preferably, about 0.01 to 75 µmol/l, about 0.05 to 50 µmol/l, about 1 to 10 µmol/l, about 0.01 to 10 µmol/l, about 0.05 to 10 µmol/l, about 0.075 to 10 µmol/l, about 0.1 to 10 mol/l, about 0.5 to 10 µmol/l, about 0.75 to 10 µmol/l, about 1.0 to 10 µmol/l, about 1.25 to 10 µmol/l, about 1.5 to 10 µmol/l, about 1.75 to 10 µmol/l, about 2.0 to 10 mol/l, about 2.5 to 10 µmol/l, about 3.0 to 10 µmol/l, about 4.0 to 10 µmol/l, about 5.0 to 10 µmol/l, about 6.0 to 10 µmol/l, about 7.0 to 10 µmol/l, about 8.0 to 10 µmol/l, about 9.0 to 10 mol/l, about 0.01 to 50 µmol/l, about 0.05 to 5.0 µmol/l, about 0.075 to 5.0 µmol/l, about 0.1 to 5.0 mol/l, about 0.5 to 5.0 µmol/l, about 0.75 to 5.0 µmol/l, about 1.0 to 5.0 mol/l, about 1.25 to 5.0 mol/l, about 1.5 to 5.0 µmol/l, about 1.75 to 5.0 mol/l, about 2.0 to 5.0 µmol/l, about 2.5 to 5.0 µmol/l, about 3.0 to 5.0 µmol/l, about 4.0 to 5.0 µmol/l, about 0.01 to 3.0 µmol/l, about 0.05 to 3.0 µmol/l, about 0.075 to 3.0 µmol/l, about 0.1 to 3.0 mol/l, about 0.5 to 3.0 µmol/l, about 0.75 to 3.0 µmol/l, about 1.0 to 3.0 mol/l, about 1.25 to 3.0 mol/l, about 1.5 to 3.0 µmol/l, about 1.75 to 3.0 mol/l, about 2.0 to 3.0 µmol/l, about 0.01 to 1.0 µmol/l, about 0.05 to 1.0 µmol/l, about 0.075 to 1.0 mol/l, about 0.1 to 1.0 µmol/l, about 0.5 to 1.0 µmol/l, about 0.75 to 1.0 mol/l, about 0.09 to 35 µmol/l, and about 0.09 to 3.2 µmol/l, and more preferably can include, but not limited to, about 0.05 to 1.0 µmol/l, about 0.075 to 1.0 µmol/l, about 0.1 to 1.0 µmol/l, about 0.5 to 1.0 mol/l, and about 0.75 to 1.0 µmol/1.

In a preferable embodiment, a TGF-beta signal inhibiting agent used includes 4-[4-(1,3-benzodioxol-5-yl)2-pyridinyl)-1H-imidazol-2-yl]benzamide or a pharmaceutically acceptable salt thereof.

In another preferred embodiment, the TGF-beta signal inhibiting agent used in the present invention includes BMP-7. This is because fibrosis was suppressed, and moreover, it was indicated that the protein in charge of the normal functions was retained, and transplant to primates was bearable. In a preferred embodiment, BMP-7 is included to be present at a concentration of about 10 ng/ml to about 1,000 ng/ml in use, and more preferably, included to be present at a concentration of about 100 ng/ml to about 1,000 ng/ml in use. BMP-7 may be included to be present at a concentration of about 100 ng/ml in use, or may be included to be present at a concentration of about 1,000 ng/ml.

A medicament for treating or preventing according to the present invention may comprise an additional medicinal component. Representative examples of such medicinal products include Rho kinase inhibiting agents and steroids. Without wishing to be bound by any theory, it is because inclusion of a Rho kinase inhibiting agent promotes adhesion of a corneal endothelial cell to prevent the cell from shedding, it enables the formation of a corneal endothelial cell layer having good cell morphology and high cell density, and thereby an effect of a TGF-β signal inhibiting agent can be enhanced. In the present invention, one type of Rho kinase inhibiting agent can be included alone, or several types thereof can be used in combination and included as necessary.

Examples of Rho kinase inhibiting agents that may be used in the present invention include compounds disclosed in the following documents: U.S. Pat. No. 4,678,783, Japanese Patent No. 3421217, International Publication No. WO 95/28387, International Publication No. WO 99/20620, International Publication No. WO 99/61403, International Publication No. WO 02/076976, International Publication No. WO 02/076977, International Publication No. WO 2002/083175, International Publication No. WO 02/100833, International Publication No. WO 03/059913, International Publication No. WO 03/062227, International Publication No. WO 2004/009555, International Publication No. WO 2004/022541, International Publication No. WO 2004/108724, International Publication No. WO 2005/003101, International Publication No. WO 2005/039564, International Publication No. WO 2005/034866, International Publication No. WO 2005/037197, International Publication No. WO 2005/037198, International Publication No. WO 2005/035501, International Publication No. WO 2005/035503, International Publication No. WO 2005/035506, International Publication No. WO 2005/080394, International Publication No. WO 2005/103050, International Publication No. WO 2006/057270, International Publication No. WO 2007/026664 and the like. Such compounds each can be manufactured by the methods described in the documents in which the respective compounds are disclosed. The specific examples can include 1-(5-isoquinolinesulfonyl)homopiperazine or a salt thereof (e.g., Fasudil (1-(5-isoquinolinesulfonyl)homopiperazine)), (R)-(+)-trans-(4-pyridyl)-4-(1-aminoethyl)-cyclohexanecarboxamide or a salt thereof (e.g., Y-27632 ((R)-(+)-trans-(4-pyridyl)-4-(1-aminoethyl)-cyclohexanecarboxamide dihydrochloride monohydrate) and the like) and the like.

The concentration of the Rho kinase inhibiting agent in the present invention is normally about 1 to 100 µmol/l, preferably, about 5 to 20 µmol/l, and more preferably about 10 µmol/l; when several types thereof are used, the concentration may be changed appropriately, and examples of other concentration ranges are normally about 0.001 to 100 µmol/l, preferably, about 0.01 to 75 µmol/l, about 0.05 to 50 mol/l, about 1 to 10 µmol/l, about 0.01 to 10 µmol/l, about 0.05 to 10 µmol/l, about 0.075 to 10 µmol/l, about 0.1 to 10 µmol/l, about 0.5 to 10 mol/l, about 0.75 to 10 µmol/l, about 1.0 to 10 µmol/l, about 1.25 to 10 µmol/l, about 1.5 to 10 mol/l, about 1.75 to 10 µmol/l, about 2.0 to 10 µmol/l, about 2.5 to 10 µmol/l, about 3.0 to 10 µmol/l, about 4.0 to 10 µmol/l, about 5.0 to 10 µmol/l, about 6.0 to 10 mol/l, about 7.0 to 10 µmol/l, about 8.0 to 10 µmol/l, about 9.0 to 10 mol/l, about 0.01 to 50 mol/l, about 0.05 to 5.0 µmol/l, about 0.075 to 5.0 µmol/l, about 0.1 to 5.0 µmol/l, about 0.5 to 5.0 µmol/l, about 0.75 to 5.0 µmol/l, about 1.0 to 5.0 mol/l, about 1.25 to 5.0 µmol/l, about 1.5 to 5.0 µmol/l, about 1.75 to 5.0 µmol/l, about 2.0 to 5.0 µmol/l, about 2.5 to 5.0 µmol/l, about 3.0 to 5.0 µmol/l, about 4.0 to 5.0 mol/l, about 0.01 to 3.0 µmol/l, about 0.05 to 3.0 µmol/l, about 0.075 to 3.0 µmol/l, about 0.1 to 3.0 µmol/l, about 0.5 to 3.0 µmol/l, about 0.75 to 3.0 µmol/l, about 1.0 to 3.0 mol/l, about 1.25 to 3.0 µmol/l, about 1.5 to 3.0 µmol/l, about 1.75 to 3.0 µmol/l, about 2.0 to 3.0 µmol/l, about 0.01 to 1.0 µmol/l, about 0.05 to 1.0 µmol/l, about 0.075 to 1.0 mol/l, about 0.1 to 1.0 µmol/l, about 0.5 to 1.0 µmol/l, about 0.75 to 1.0 µmol/l, about 0.09 to 35 µmol/l, and about 0.09 to 3.2 µmol/l, and more preferably can include, but not limited to about 0.05 to 1.0 µmol/l, about 0.075 to 1.0 µmol/l, about 0.1 to 1.0 mol/l, about 0.5 to 1.0 mol/l, and about 0.75 to 1.0 mol/l.

The present invention can be administered as eye-drops.

The dosage amount and the frequency of administration vary in accordance with symptoms, ages, weights or administration forms. In case of the use as an eye lotion, for example, for normal adults, the formulation, containing an effective ingredient of about 0.0001 to 0.1 w/v %, and preferably about 0.003 to 0.03 w/v %, can be administered 1 to 10 times per day, preferably 1 to 6 times per day, and more preferably 1 to 3 times per day, and at the amount in the range of about 0.01 to 0.1 mL per time. When the medicament according to the present invention is introduced into an anterior chamber, the medicament at a concentration one-tenth to one-thousandth of the above-mentioned concentration can be used. Those skilled in the art can appropriately select the type and concentration of TGF-beta signal inhibiting agent, Rho kinase inhibiting agent, and the like in accordance with disease states.

In another aspect, the present invention provides a TGF-beta signal inhibitory substance for treatment or prevention of a disorder associated with extracellular matrix (ECM) abnormality in a corneal endothelium. A TGF-beta signal inhibitory substance can be used interchangeably with a TGF-beta signal inhibiting agent. In this use, with regard to the extracellular matrix (ECM) abnormality in a corneal endothelium and the TGF-beta signal inhibiting agent, any embodiments described herein can be used.

In another aspect, the present invention provides a method for treating or preventing a disorder associated with extracellular matrix (ECM) abnormality in a corneal endothelium in a subject, wherein the method comprises a step of administering an effective amount of a TGF-beta signal inhibiting agent to the subject. In this method, with regard to the extracellular matrix (ECM) abnormality in a corneal endothelium and the TGF-beta signal inhibiting agent, any embodiments described herein can be used.

The subject of the administration (transplantation) of the medicament or method according to the present invention includes mammals (e.g., humans, mice, rats, hamsters, rabbits, cats, dogs, cows, horses, sheep, monkeys, and the like), and the subject is preferably primates, and particularly preferably humans. Therapy for corneal endothelium in primates had not achieved sufficient results before, and from that point of view, the present invention provides an innovative therapeutic method and medicament.

Reference literatures such as scientific literatures, patents, and patent applications cited herein are incorporated herein by reference to the same extent that the entirety of each document is specifically described.

As described above, the present invention has been illustrated by showing preferable embodiments to facilitate understanding. The present invention is illustrated below based on Examples. The aforementioned illustration and the following Examples are not provided for the purpose of limiting the present invention, but for the sole purpose of exemplification. Thus, the scope of the present invention is not limited to embodiments and Examples specifically described herein and is limited only by the scope of claims.

EXAMPLES

Hereinafter, examples of normally culturing a cell of a corneal endothelial cell according to the present invention will be described. In applicable, standards stipulated by Ministry of Health, Labour and Welfare, Ministry of Education, Culture, Sports, Science and Technology, or the like were recognized for the handling of biological samples or the like; and if applicable, the handling was performed based on Helsinki Declaration or ethical codes prepared based on the Declaration. For the donation of eyes used for the research, agreements were obtained from close relatives of all the deceased donors. The present research was approved by the institutional review board of Erlangen university (Doyle), SightLife™ (Seattle, Wash.) eye bank, or those in accordance therewith.

In Fuchs' endothelial corneal dystrophy, corneal endothelial cells lead to cell death, and when remaining corneal endothelial cells cannot compensate a pumping function and a barrier function, then the transparency of the cornea cannot be maintained, leading to loss of sight due to corneal opacity.

In addition, it is known that a corneal endothelial cell of a Fuchs' endothelial corneal dystrophy patient overproduces an extracellular matrix to cause guttae formation and thickening of Descemet's membrane. Since the guttae formation and the thickening of Descemet's membrane cause light scattering and the like, it causes reduced visual acuity, photophobia, blurred vision to significantly injure the QOL of the patients. An immobilized corneal endothelial cell strain (iFECD) derived from Fuchs' endothelial corneal dystrophy patients was used as a model, and compared with an immobilized corneal endothelial cell strain (iHCEC) derived from healthy donors to clarify a cause relating to production of an extracellular matrix, and identify a therapy target.

Preparation Example

Production of an Immobilized Corneal Endothelial Cell Strain (iFECD) Model Derived from a Fuchs' Endothelial Corneal Dystrophy Patient In the present example, immobilized corneal endothelial cell strains (iFECD) from corneal endothelial cells derived from a Fuchs' endothelial corneal dystrophy patient were produced.
(Culture Method)
Corneal endothelial cells were mechanically peeled off with a basal membrane from a corneal for research purchased from the Seattle Eye Bank. After collagenase was used to detach and collect the corneal endothelial cell from the basal membrane, the cells were subjected to primary culture. With regard to a medium, Opti-MEM I Reduced-Serum Medium, Liquid (INVITROGEN catalog No.: 31985-070) to which 8% FBS (BIOWEST, catalog No.: S1820-500), 200 mg/ml $CaCl_2.2H_2O$ (SIGMA catalog No.: C7902-500G), 0.08% chondroitin sulfate (SIGMA catalog No.: C9819-5G), 20 μg/ml ascorbic acid (SIGMA catalog No.: A4544-25G), 50 μg/ml gentamicin (INVITROGEN catalog No.: 15710-064) and 5 ng/ml EGF (INVITROGEN catalog No.: PHG0311) were added and that was acclimated for a 3T3 feeder cell, was used as a basal medium. Further, the cells were cultured in a basal medium to which SB431542 (1 μmol/l) and SB203580 (4-(4-fluorophenyl)-2-(4-methylsulfonylphenyl)-5(4-pyridyl)imidazole<4-[4-(4-fluorphenyl)-2-(4-methylsulfinylphenyl)-1H-imidazol-5-yl] pyridine) (1 μmol/l) were added (referred to as "SB203580+SB431542+3T3 acclimated medium").
(Method of Acquisition)
Corneal endothelial cells from three human patients that led to bullous keratopathy by clinical diagnosis of Fuchs' endothelial corneal dystrophy and underwent corneal endothelial transplantation (Descemet membrane endothelial keratoplasty=DMEK) were obtained under the written consent and the approval of Ethics Committee. In DMEK, mechanically pathological corneal endothelial cells and Descemet membrane, which is a basement membrane, were exfoliated together and immersed in Optisol-GS (Bausch & Lomb Incorporated), which is a corneal storage solution. After that, collagenase treatment was carried out to enzymatically collect corneal endothelial cells, which was then cultured in SB203580+SB431542+3T3-conditioned medium. With regard to the cultured corneal endothelial cells derived from Fuchs' endothelial corneal dystrophy patients, SV40 large T antigen and hTERT genes were amplified by PCR and introduced into a lentiviral vector (pLenti6.3_V5-TOPO; Life Technologies Inc.). The lentiviral vector was then used to infect 293T cells (RCB2202;

Riken Bioresource Center, Ibaraki, Japan) by a transfection reagent (Fugene HD; Promega Corp., Madison, Wis.), together with three types of helper plasmids (pLP1, pLP2, pLP/VSVG; Life Technologies Inc.). Culture supernatant comprising viruses was collected after 48 hours from the infection. It is added using 5 µg/ml polybrene to culture solutions of cultured corneal endothelial cells derived from Fuchs' endothelial corneal dystrophy patients to introduce SV40 large T antigen and hTERT genes. Phase-contrast microscope images of an immobilized corneal endothelial cell strain (iFECD) derived from Fuchs' endothelial corneal dystrophy patients were confirmed. Corneal endothelial cells cultured from a cornea for research imported as a control from a Seattle eye bank were immobilized by a similar method to make an immobilized cell strain (iHCEC) of normal corneal endothelial cell. When seeing phase-contrast microscope images of an immobilized corneal endothelial cell strain (iHCEC) derived from healthy donors, and an immobilized corneal endothelial cell strain (iFECD), both of the iHCEC and the iFECD have the same one-layered polygonal form as a normal corneal endothelial cell. In the cases of the iHCEC and the iFECD, SB431542 of which maintenance culture was carried out in DMEM+10% FBS was obtained from TOCRIS Corporation (Catalog number: 1614). SB203580 was obtained from CALBIOCHEM (Catalog number: 559389).

Preparation Example 2

Confirmation of the Normal Functions of an Immobilized Corneal Endothelial Cell Strain (iFECD)

In the present example, the normal function of an immobilized corneal endothelial cell strain (iFECD) was confirmed.
(Immunostaining with $Na^+/K^+$-ATPase and ZO-1)
At first, in order to confirm the normal functions of an immobilized corneal endothelial cell strain (iFECD), immunostaining with $Na^+/K^+$-ATPase and ZO-1 was carried out. It is to confirm a pumping function and a barrier function, which are functions of a corneal endothelial cell. $Na^+/K^+$-ATPase and ZO-1 each exhibit the normality of a pumping function and a barrier function, which are functions of a corneal endothelial cell. A technique is as follows.
(Cell Observation Method Including Staining and the Like (Histological Test))
Cells were observed under a phase-contrast microscope. In addition, after cells were fixed, ZO-1 and $Na^+/K^+$-ATPase were used as function-related markers to carry out immunostaining and observation under a fluorescence microscope. For a tissue staining test, cultured cells are put in Lab-Tek™ Chamber Slides™ (NUNC A/S, Roskilde, Denmark), and then fixed at room temperature (RT) for 10 minutes in 4% formaldehyde, and incubated with 1% bovine serum albumin (BSA) for 30 minutes. Specifically, cultured cells on Lab-Tek™ Chamber Slides™ (NUNC A/S, Roskilde, Denmark) are fixed at room temperature for 10 minutes in 4% formaldehyde, and then incubated with 1% bovine serum albumin (BSA) for 30 minutes. In order to examine the expression type of the cells, ZO-1 (Zymed Laboratories, Inc., South San Francisco, Calif.), which is a tight junction-related protein, and $Na^+/K^+$-ATPase (Upstate Biotec, Inc., Lake Placid, N.Y.), which is a pumping function-related protein, were immunohistochemically analyzed. ZO-1 and $Na^+/K^+$-ATPase were used as markers relating to cell functions. Staining of ZO-1 and $Na^+/K^+$-ATPase were carried out using 1:200 dilutions of a ZO-1 polyclonal antibody and a $Na^+/K^+$-ATPase monoclonal antibody, respectively. For a secondary antibody, 1:2000 dilution of Alexa Fluor (registered trademark) 488 labeled, or Alexa Fluor (registered trademark) 594 labeled goat anti-mouse IgG (Life Technologies) was used. Cell nuclei were then stained with DAPI (Vector Laboratories, Inc., Burlingame, Calif.) or PI (Sigma-Aldrich). A slide was then observed under a fluorescence microscope (TCS SP2 AOBS; Leica Microsystems, Welzlar, Germany).

When seeing the result, both of the iHCEC and the iFECD expressed $Na^+/K^+$-ATPase and ZO-1 in all the cells, and it was shown that the immobilized cell strain made maintained the normal functions.

In addition, morphological observation images of the iHCEC and the iFECD under a transmission electron microscope are shown. The iHCEC and the iFECD were cultured in DMEM on Transwell without serum. One week later, they were fixed in a confluent state and when the morphology was observed under a transmission electron microscope, they were shown to be one-layered cells that are not recognized to have morphologically apparent abnormality.

In addition, it is known that a corneal endothelial cell of a Fuchs' endothelial corneal dystrophy patient overproduces an extracellular matrix to cause guttae formation and thickening of Descemet's membrane. Accordingly, with regard to expression of collagen type I, collagen type IV, and Fibronectin, which are proteins constituting an extracellular matrix, the iHCEC and the iFECD were cultured on culture dishes and immunostained. In the iFECD, it was shown that expression of collagen type I, collagen type IV, and Fibronectin was increased in comparison with the iHCEC. In addition, when the gene expression level of the cultured iHCEC and iFECD was examined by a real-time PCR method, it was recognized that collagen type I and Fibronectin significantly promoted the expression level, and that collagen type IV tended to promote the expression.

It was examined whether the iFECD overproduces an extracellular matrix in the same way as a corneal endothelium of Fuchs' endothelial corneal dystrophy patients. The iHCEC and the iFECD were cultured in DMEM on Transwell without serum, one week after which they were fixed in a confluent state and HE-stained. In the iFECD, it was recognized that a significantly thickened extracellular matrix was produced in comparison with the iHCEC. As described above, a disease model cell was made which has a characteristic of overproduction of an extracellular matrix in Fuchs' endothelial corneal dystrophy patients. Since analysis using the disease model cell is expected to contribute to clarifying the pathological condition of Fuchs' endothelial corneal dystrophy, for which there are many unclear points, this cell was used to try the development of a therapeutic medicament for Fuchs' endothelial corneal dystrophy in the following.

Example 1

Real-Time PCR Analysis of the Expression Amount of a Gene Related to Epithelial-Mesenchymal Transition (EMT) Related to Production of an Extracellular Matrix With regard to the iHCEC and the iFECD, the present example shows a result of analyzing, by real-time PCR, the expression amount of a gene related to epithelial-mesenchymal transition (EMT) related to production of an extracellular matrix.

(Real-Time PCR)

Real-time PCR method: In addition, PCR was performed by a Taqman method for Snail1, Snail2, or ZEB1 in accordance with the following method. A Taqman probe was purchased from INVITROGEN. The mRNA amount of collagen type I, collagen type IV, and Fibronectin was examined by a real-time PCR method. RNEasy (QIAGEN, Catalog number: 74106) was used in extraction of the total RNA from cells. The extracted RNA was subjected to a reverse transcription reaction (42° C., 60 minutes) with ReverTra Ace (TOYOBO Co., Ltd., Catalog number: TRT-101), and collagen type I, collagen type IV, and Fibronectin were amplified with a reaction reagent TaqMan Fast Advanced mastermix (Applied Biosystems) using GAPDH as an internal standard. Probes (a labeled primer set available from Applied Biosystems) described below was used in the PCR reaction, which was performed in the StepOne™ (Applied Biosystems) real-time PCR system.
Snail1 Hs00195591 ml SNAI1
Snail2 Hs00950344 ml SNAI2
ZEB1 Hs00232783 ml ZEB1
GAPDH TaqMan® pre developed Assay Reagents Human GADPH (cat no.: 4333764F).

(Result)

The result is shown in FIG. 1. As shown in FIG. 1, when the expression amount of a gene related to epithelial-mesenchymal transition (EMT) related to production of an extracellular matrix was analyzed by real-time PCR, it was recognized in Snail1 and ZEB1 that the iFECD significantly promoted the expression in comparison with the iHCEC.

(Promotion of Expression of Snail1 and ZEB1 by the TGF-Beta)

In order to confirm whether expression promotion of Snail1 and ZEB1 relates to production of an extracellular matrix, stimulation with TGF-beta, which is known to accelerate expression of Snail1 and ZEB1, was performed. The technique is as described below. The iFECD and the iHCEC were cultured in DMEM containing 10% fetal bovine serum, and cultured overnight in DMEM without 10% fetal bovine serum. After that, expression of Snail1, ZEB1, collagen type I, collagen type IV, collagen type VIII, Fibronectin was examined by a real-time PCR method. Probes described below were used in the PCR reaction, which was performed in the StepOne™ (Applied Biosystems) real-time PCR system.
Snail1 Hs00195591_ml SNAI1
ZEB1 Hs00232783_ml ZEB1
collagen type I Hs00164004_COL1A1
collagen type IV Hs00266327_ml COL4A1
collagen type VIII Hs00697025_ml COL8A2
Fibronectin Hs01549976_ml FN1
GAPDH TaqMan® pre developed Assay Reagents Human GADPH (cat no.: 4333764F).

Figure 2:
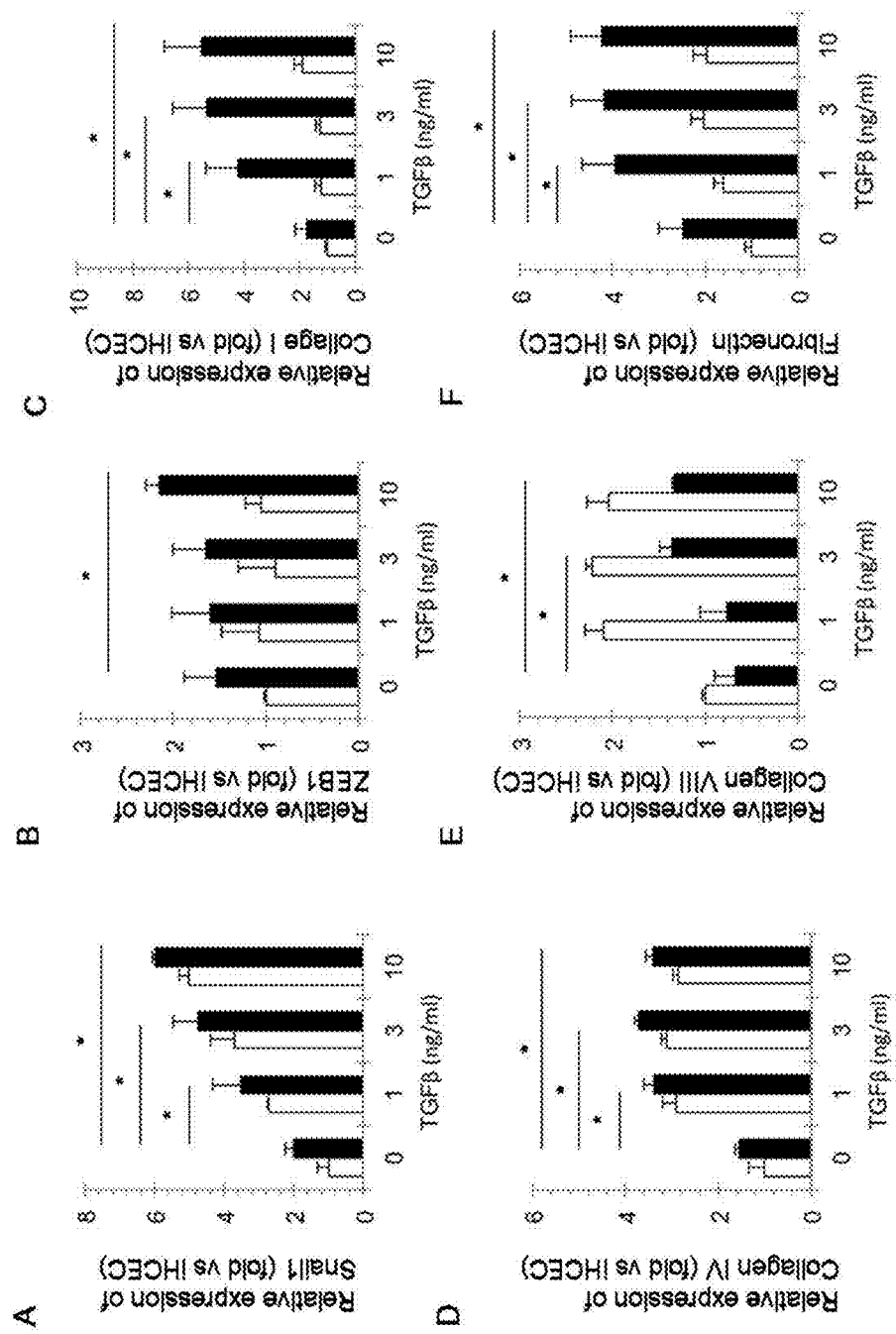
FIG. 2 shows a state that TGF-beta increases expression of Snail1, ZEB1, and in vitro matrix-constituting proteins.

The result is shown in FIG. 2. It was confirmed that TGF-beta significantly accelerates expression of Snail1 and ZEB1 in the iFECD (A, B). Accordingly, when the gene expression amount of a protein constituting an extracellular matrix was analyzed by real-time PCR, expression of collagen type I, collagen type IV, collagen type VIII, and Fibronectin was significantly accelerated.

Example 2

Acceleration of an iFECD-Produced Extracellular Matrix by TGF-Beta

In the present example, it was examined whether an iFECD-produced extracellular matrix was accelerated by TGF-beta.

The iHCEC and the iFECD were cultured in DMEM on Transwell without serum, one week after which they were fixed in a confluent state and HE-stained. The procedure is as described below. If required, deparaffinization (for example, with pure ethanol) and water washing were carried out, and the sample was immersed in hematoxylin from Omni for 10 minutes. Thereafter, water washing with running water was performed, and ammonia water was used for developing color for 30 seconds. Thereafter, water washing with running water for 5 minutes, staining for 2 minutes with a ten-fold diluted solution of eosin hydrochloride, dehydration, lucidification, and mounting were performed. It was recognized in the iHCEC and the iFECD that TGF-beta stimulation produced a significantly thickened extracellular matrix. Further, it was recognized that in the presence of TGF-beta, the iFECD produced a significantly thickened extracellular matrix in comparison with the iHCEC.

These show that in corneal endothelial cells of Fuchs' endothelial corneal dystrophy patients, the expression level of Snail1 and ZEB1 is high and that the production quantity of an extracellular matrix in response to the TGF-beta stimulation is significantly higher than corneal endothelial cells of a healthy subject.

Example 3

An Effect on the Extracellular Matrix Production by Suppression of Snail1 and ZEB1 Using siRNA In the present example, an effect on the extracellular matrix production by suppression of Snail1 and ZEB1 using siRNA was examined in order to demonstrate that the expression promotion of Snail1 and ZEB1 causes production of an extracellular matrix. The experimental procedure is as described below.

(Technique)

The iFECD and the iHCEC were seeded and incubated with Snail1 Stealth RNAi™ (Life Technologies Corp., Carlsbad, Calif.) or ZEB1 Stealth RNAi™ (Life Technologies Corp., Carlsbad, Calif.) and Lipofectamine™ RNAiMAX (Life Technologies Corp., Carlsbad, Calif.) at 37° C. for 12 hours. A random sequence of RNAi was used as a control. Thereafter, cells was passaged and used in the experiment. Three types of each of Snail1 Stealth RNAi™ and ZEB1 Stealth RNAi™ were used to carry out the experiment, and representative examples were shown as the results. Cells in which Snail1 or ZEB1 was knocked down by siRNA were seeded, and expression of Snail1, ZEB1, collagen type I, collagen type IV, collagen type VIII, and Fibronectin was examined by a real-time PCR method. Probes described below were used in the PCR reaction, which was performed in the StepOne™ (Applied Biosystems) real-time PCR system.

(Material)

siRNA
siRNA of Snail1 (SNAI1 HSS143995*, SNAI1 HSS143996, SNAI1 HSS143997)
siRNA of ZEB1 (ZEB1 HSS110548*, ZEB1 HSS110549, ZEB1 HSS186235)
It should be noted that siRNA shown in the result was described as *.
Probes in a Real-Time PCR Method
Snail1 Hs00195591_ml SNAI1
ZEB1 Hs00232783_ml ZEB1
Collagen type I Hs00164004_ml COL1A1
Collagen type IV Hs00266327_ml COL4A1

Collagen type VIII Hs00697025_m1 COL8A2

Fibronectin Hs01549976_m1 FN1

GAPDH TaqMan® pre developed Assay Reagents Human GADPH (cat no.: 4333764F).

(Result)

Figure 4:
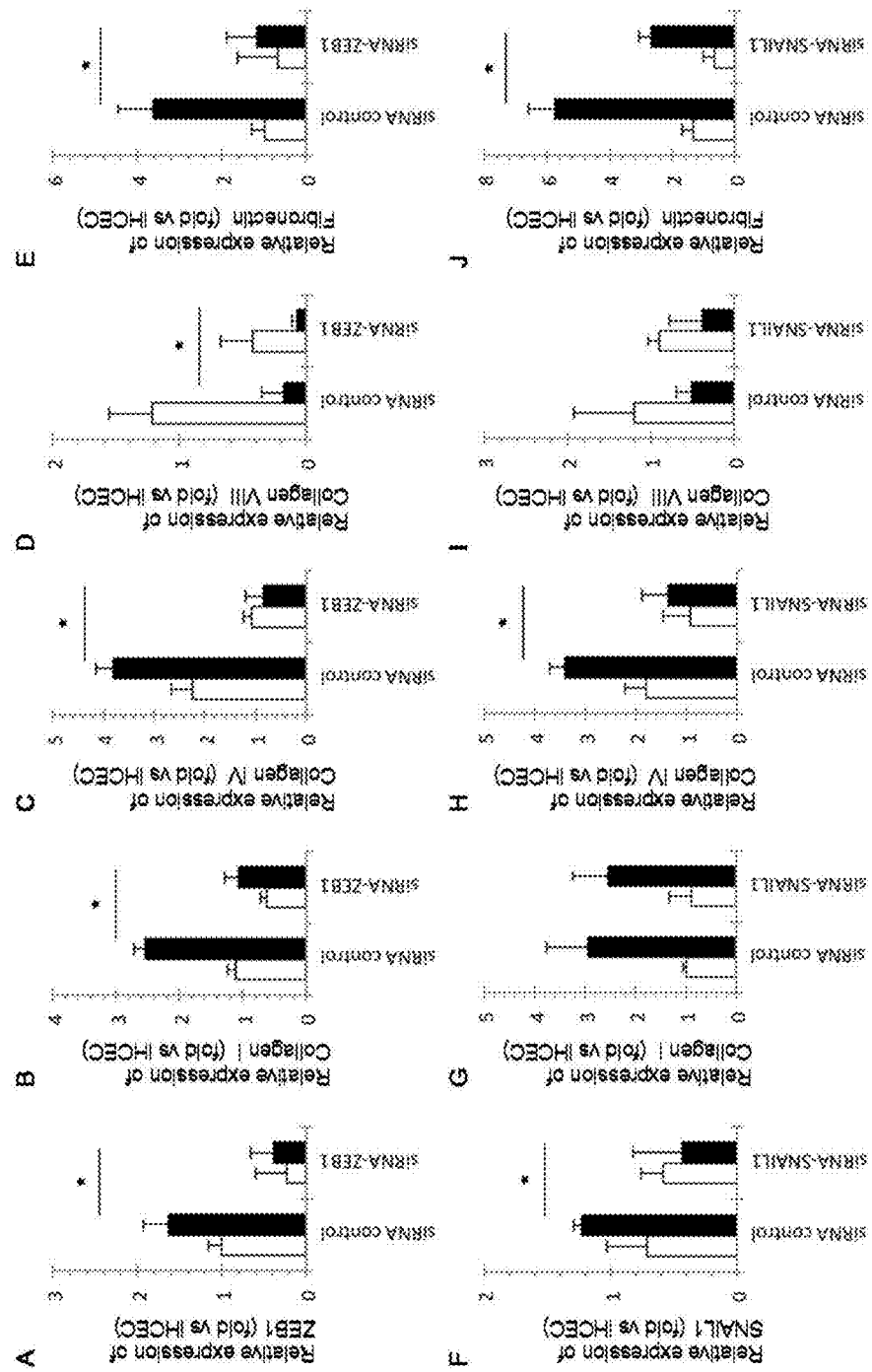
FIG. 4 shows that ZEB1 and Snail1 negatively control the gene expression of an in vitro matrix-constituting protein.

The result is shown in FIG. 4. It was confirmed that siRNA suppresses expression of Snail1 and ZEB1 (A, F). The expression suppression of Snail1 or ZEB1 by siRNA significantly suppressed expression of collagen type I, collagen type IV, collagen type VIII, and Fibronectin. From this result, it was found that ZEB1 or Snail1 negatively controls gene expression of an extracellular-constituting protein.

(Adjustment of Expression of Collagen Type I, Collagen Type IV, and Fibronectin by Immunostaining)

It was then confirmed by immunostaining that expression of collagen type I, collagen type IV, and Fibronectin was suppressed. The technique of immunostaining is similar to the above-described Preparation Example 2. With regard to an antibody, antibodies against collagen type I, collagen type IV, and Fibronectin were used instead to carry out the experiment.

An antibody against collagen type I: Anti collagen type I (Rabbit polyclonal) (ROCKLLAND™ antibodies and assays, Cat no.: 600-401-103S)

An antibody against collagen type IV: collagen type IV (Rabbit polyclonal) (Abcam, Cat no.: ab6586)

An antibody against Fibronectin: Anti-fibronectin (mouse monoclonal) (BD Biosciences, Cat no.: 610077)

For a tissue staining test, cultured cells were put in Lab-Tek™ Chamber Slides™ (NUNC A/S, Roskilde, Denmark), fixed with 4% formaldehyde for 10 minutes at room temperature (RT), and incubated with 1% bovine serum albumin (BSA) for 30 minutes. Specifically, cultured cells on Lab-Tek™ Chamber Slides™ (NUNC A/S, Roskilde, Denmark) were fixed at room temperature for 10 minutes in 4% formaldehyde, and then incubated with 1% bovine serum albumin (BSA) for 30 minutes. In order to examine expression of an extracellular matrix produced by cells, a 1:200 dilution of each of antibodies against collagen type I, collagen type IV, and Fibronectin was used to carry out. For a secondary antibody, a 1:2000 dilution of Alexa Fluor (registered trademark) 488 labeled, or Alexa Fluor (registered trademark) 594 labeled goat anti-mouse IgG (Life Technologies) was used. Cell nuclei were then stained with DAPI (Vector Laboratories, Inc., Burlingame, Calif.) or PI (Sigma-Aldrich). A slide was then observed under a fluorescence microscope (TCS SP2 AOBS; Leica Microsystems, Welzlar, Germany).

(Result)

Figure 5:
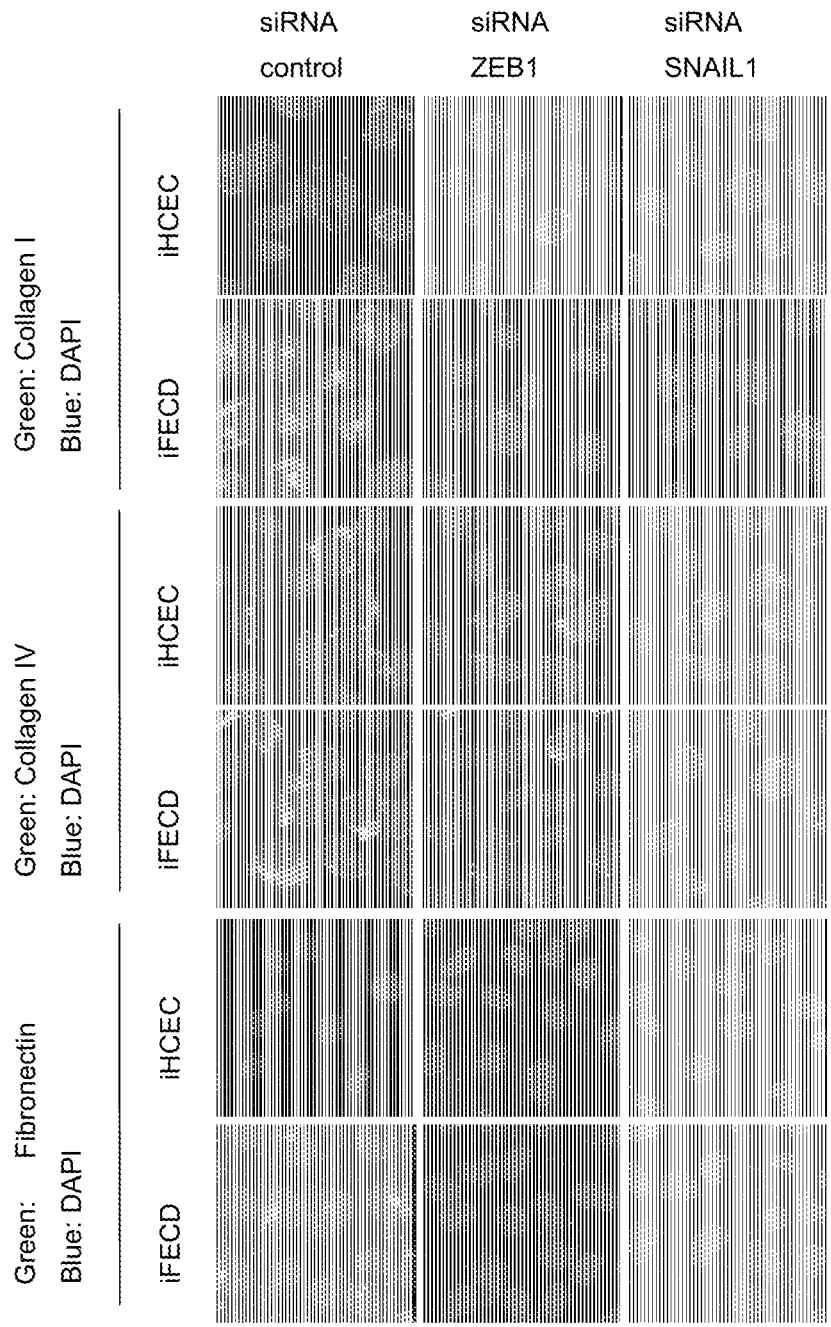
FIG. 5 shows a state that ZEB1 or Snail1 negatively control expression of in vitro matrix-constituting proteins.

The result is shown in FIG. 5. As shown in FIG. 5, it was also confirmed that expression suppression of Snail1 or ZEB1 by siRNA also suppressed expression of collagen type I, collagen type IV, collagen type VIII, and Fibronectin at a protein level.

Example 4

Suppression of Overproduction of an Extracellular Matrix in the iFECD by Expression Suppression of Snail1 or ZEB1

In the present example, it was confirmed that expression suppression of Snail1 or ZEB1 suppressed overproduction of an extracellular matrix in the iFECD.

Further, the iHCEC and the iFECD were cultured in DMEM on Transwell without serum, one week after which they were fixed in a confluent state and HE-stained. The HE-staining was carried out in accordance with the procedure of the above-described examples.

(Result)

Figure 6:
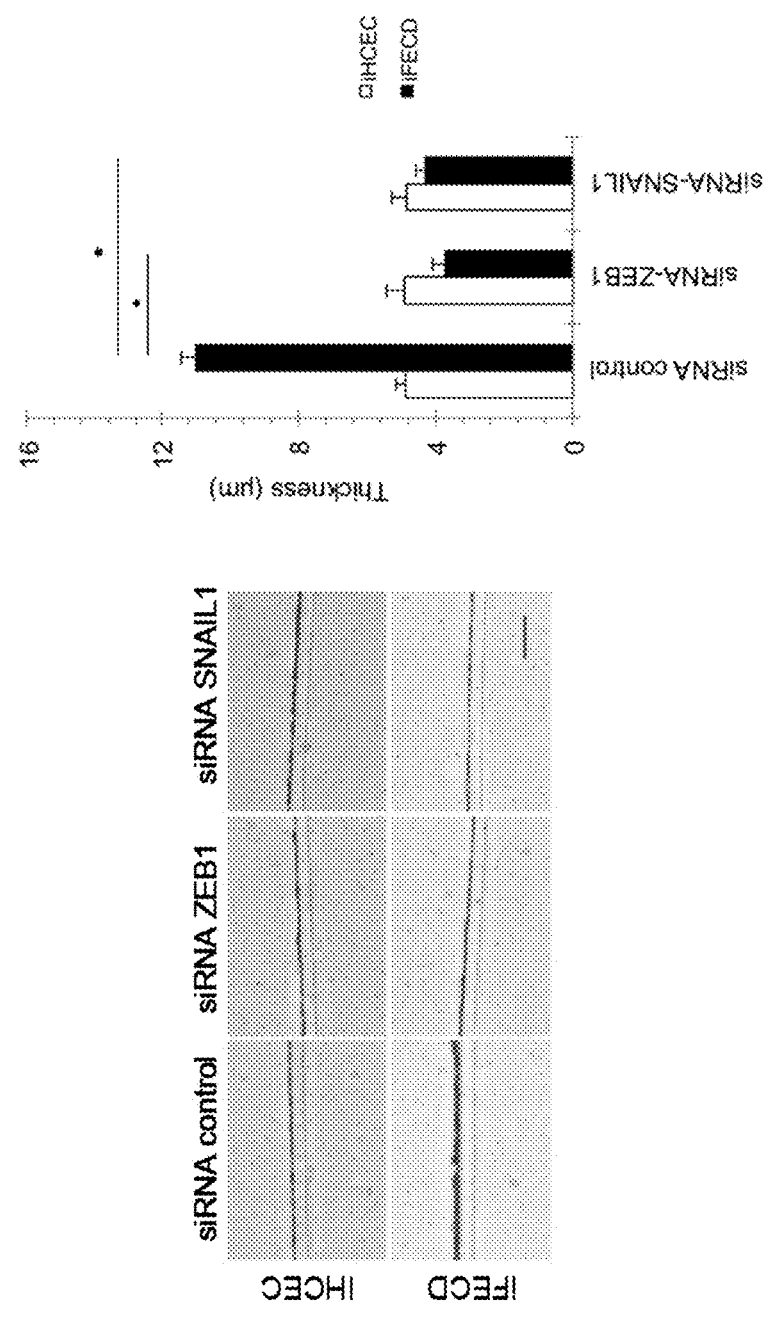
FIG. 6 shows that suppression of ZEB1 or Snail1 can suppress in vitro matrix overproduction of Fuchs' endothelial corneal dystrophy cells.

The result is shown in FIG. 6. As shown in FIG. 6, expression suppression of Snail1 or ZEB1 by siRNA suppressed overproduction of an extracellular matrix in the iFECD to result in the normal level. Accordingly, it was found that suppression of ZEB1 or Snail can suppress overproduction of an extracellular matrix in a Fuchs' endothelial corneal dystrophy cell.

Example 5

Adjustment of Extracellular Matrix Abnormality in a Corneal Endothelium by a TGF-Beta Signal Inhibiting Agent It was then examined whether a TGF-beta signal inhibiting agent, SB431542, can be used to inhibit a TGF-beta signal and adjust extracellular matrix abnormality in a corneal endothelium. SB431542 was obtained from TOCRIS Corporation (Catalog number: 1614).

(Examination by Real-Time PCR)

The gene expression amount was confirmed by real-time PCR. Real-time PCR was carried out in accordance with the above-described examples. The following probes were used for collagen type I, collagen type IV, collagen type VIII, and Fibronectin.

Collagen type I Hs00164004_m1 COL1A1

Collagen type IV Hs00266327_m1 COL4A1

Collagen type VIII Hs00697025_m1 COL8A2

Fibronectin Hs01549976_m1 FN1

GAPDH TaqMan® pre developed Assay Reagents Human GADPH (cat no.: 4333764F)

(Result)

Figure 7:
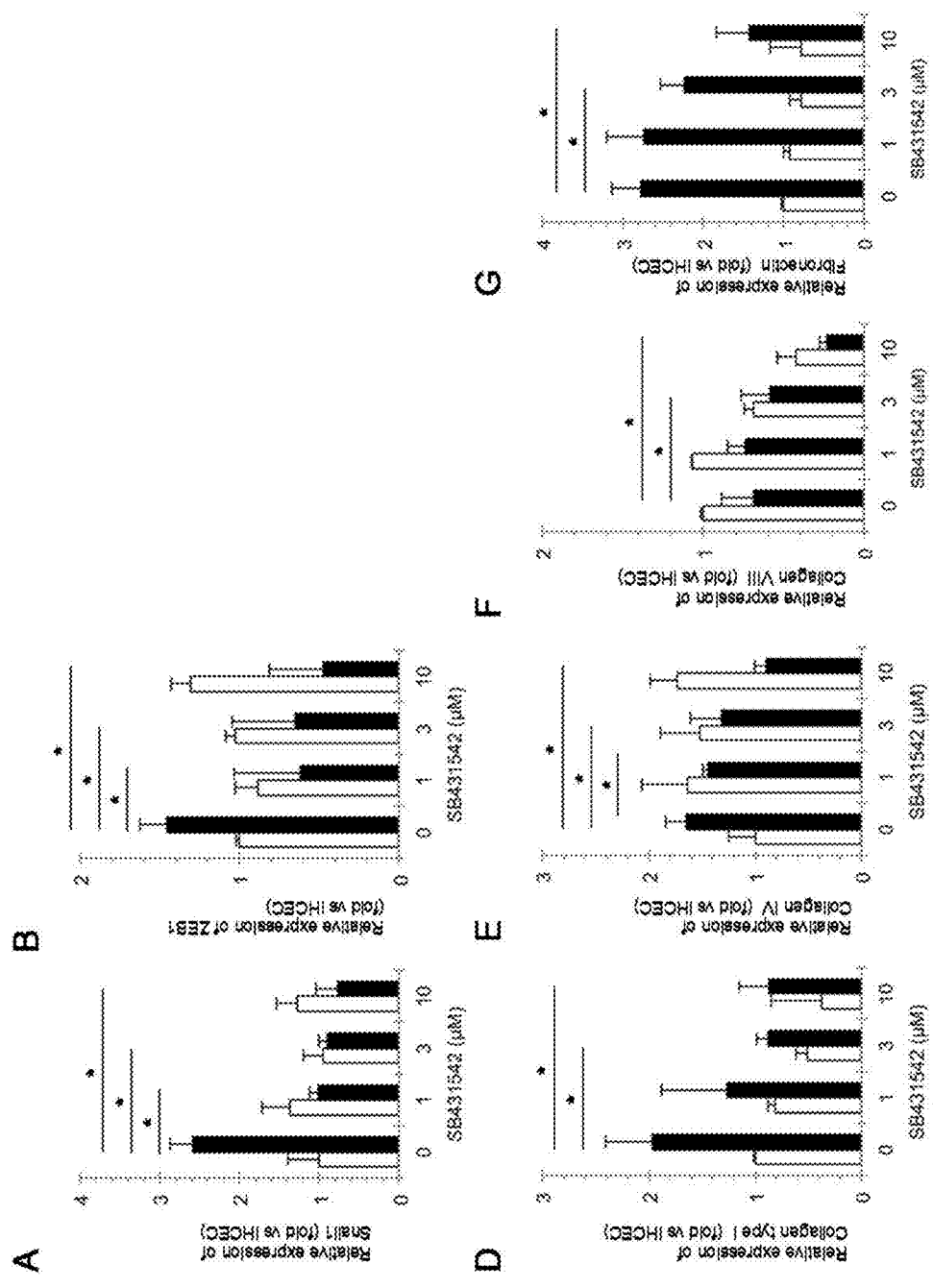
FIG. 7 shows a state that TGF-beta signal inhibition suppresses the expression of Snail1, ZEB1, and an in vitro matrix-constituting protein.

The result is shown in FIG. 7. As shown in FIG. 7, a significant decrease in the expression amount of Snail1 and ZEB1 was recognized by real-time PCR. Further, when the gene expression amount of an extracellular matrix-constituting protein in the iFCED was analyzed with SB431542 by real-time PCR, expression of collagen type I, collagen type IV, collagen type VIII, and Fibronectin was significantly suppressed.

(Examination of the Expression of Collagen Type I, Collagen Type IV, and Fibronectin by Immunostaining)

Then, expression of collagen type I, collagen type IV, and Fibronectin was similarly examined by immunostaining. The immunostaining was carried out in accordance with the above-described examples, provided that the following antibodies were used as antibodies for collagen type I, collagen type IV, and Fibronectin.

An antibody against collagen type I: Anti collagen type I (Rabbit polyclonal) (ROCKLLAND™ antibodies and assays, Cat no.: 600-401-103S)

An antibody against collagen type IV: collagen type IV (Rabbit polyclonal)(Abcam, Cat no.: ab6586)

An antibody against Fibronectin: Anti-fibronectin (mouse monoclonal) (BD Biosciences, Cat no.: 610077)

(Result)

Figure 8:
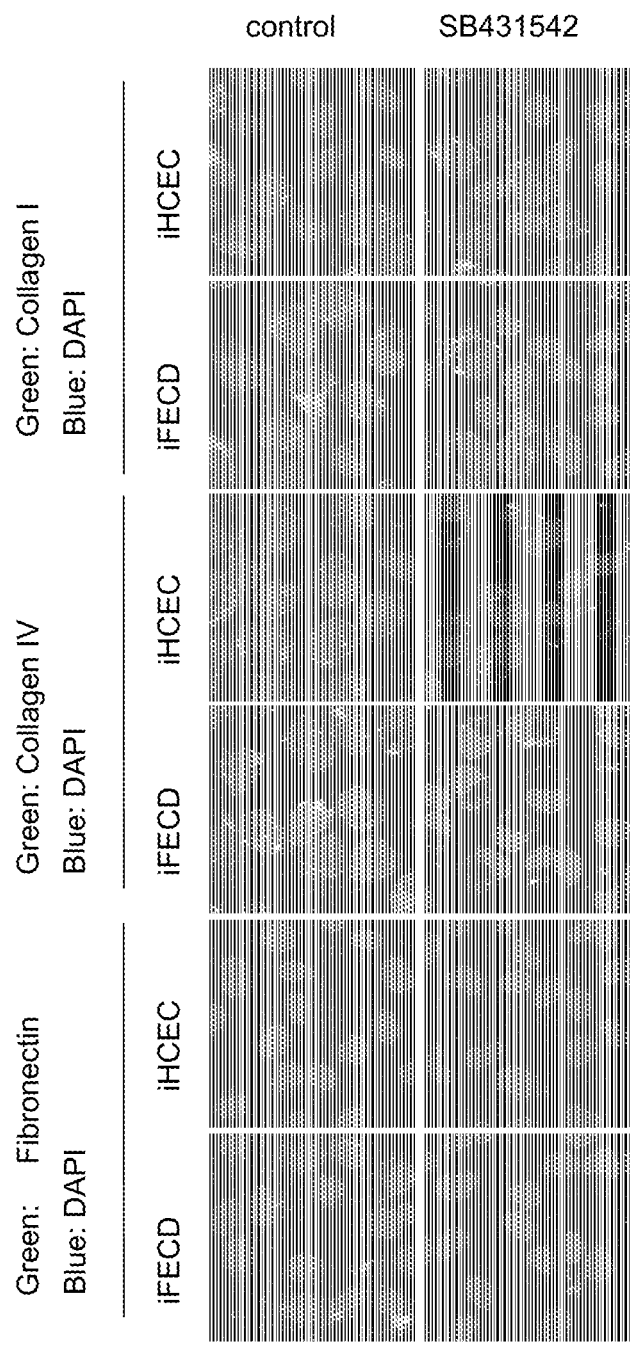
FIG. 8 shows a state that TGF-beta signal inhibition can control expression of an in vitro matrix-constituting protein.

The result is shown in FIG. 8. As shown in FIG. 8, it was confirmed that TGF-beta signal inhibition using SB431542 also suppressed expression of collagen type I, collagen type IV, collagen type VIII, and Fibronectin in a protein level.

Example 6

An Effect of a TGF-Beta Signal Inhibiting Agent in the Case of Fixing in a Confluent State One Week Later In the present example, an effect of a TGF-beta signal inhibiting agent in the case of fixing in a confluent state one week later was confirmed.

Further, the iHCEC and the iFECD were cultured on Transwell Permeable Supports: 0.4 μm, six well plates (Costar, Cat no.: 3450) without serum, one week after which they were fixed in a confluent state and HE-stained. The HE-staining was carried out in accordance with the procedure of the above-described examples.

(Result)

Figure 9:
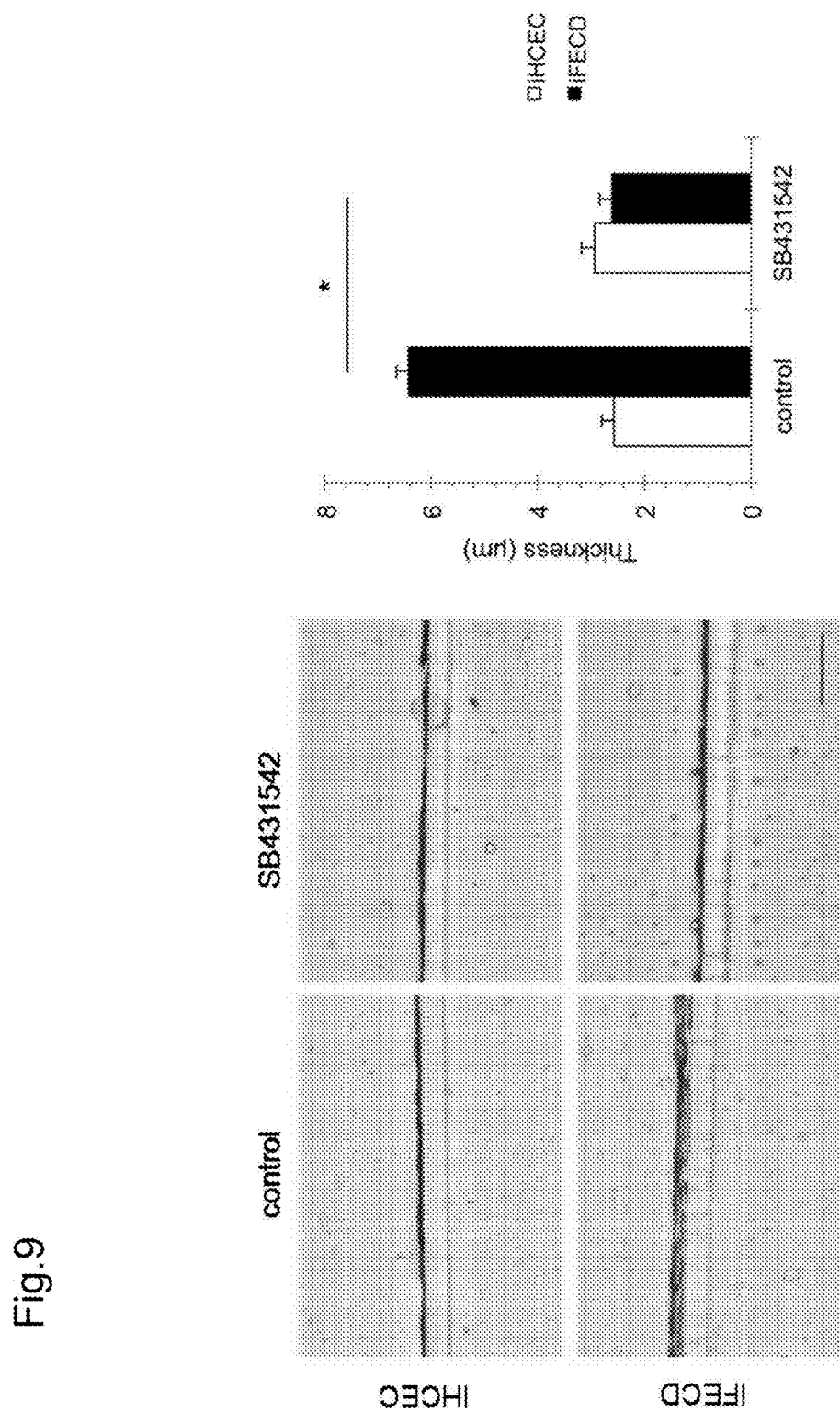
FIG. 9 shows a state that TGF-beta signal inhibition can suppress in vitro matrix overproduction of Fuchs' endothelial corneal dystrophy cells.

The result is shown in FIG. 9. As shown in FIG. 9, TGF-beta signal inhibition using SB431542 also suppressed overproduction of an extracellular matrix in the iFECD to result in the normal level.

The above description shows that a Fuchs' endothelial corneal dystrophy patient produces an excess amount of an extracellular matrix under a TGF-beta signal by promoting Snail1 or ZEB1 in comparison with a healthy subject. Further, it shows that suppression by siRNA or the like of EMT-related genes such as Snail1, ZEB1, or the like and genes related to protein production can suppress production of an extracellular matrix. In addition, it shows that inhibition of a TGF-beta signal can also suppress production of an extracellular matrix. It indicates the possibility that suppression of inhibition of a TGF-beta signal, EMT-related genes such as Snail1, ZEB1, or the like, or a signal thereof can suppress overproduction of an extracellular matrix of corneal endothelial cells of Fuchs' endothelial corneal dystrophy patients and suppress guttae formation and thickening of Descemet's membrane.

As described above, the present invention is illustrated by preferable embodiments of the present invention. However, it will be understood that the scope of the present invention should be interpreted only by the claims. It will be understood that the contents of patents, patent applications, and literatures cited in the present specification should be incorporated herein by reference as if their contents per se are specifically described in the present specification.

INDUSTRIAL APPLICABILITY

Provided are techniques available in industries (the cell-culturing industry, the pharmaceutical industry, and the like) relating to therapeutic or preventive medicaments for a disease, disorder, or condition associated with extracellular matrix (ECM) abnormality in a corneal endothelium, in particular, extracellular matrix (ECM) abnormality in Fuchs' endothelial corneal dystrophy, and photophobia, wherein the medicaments comprises a TGF-beta signal inhibiting agent.

The invention claimed is:

1. A method for treating Fuchs' endothelial corneal dystrophy or a disease, disorder, or condition related to Fuchs' endothelial corneal dystrophy, wherein the method comprises the step of:
    administering a medicament comprising an effective amount of a transforming growth factor-beta (TGF-beta) signal inhibiting agent to the subject,
    wherein the TGF-beta signal inhibiting agent alone is effective to treat Fuchs' endothelial corneal dystrophy or the disease, disorder, or condition related to Fuchs' endothelial corneal dystrophy.

2. The method according to claim 1, wherein the disease, disorder, or condition is a disorder related to Fuchs' endothelial corneal dystrophy.

3. The method according to claim 1, wherein the disease, disorder, or condition further comprises corneal opacity in Fuchs' endothelial corneal dystrophy.

4. The method according to claim 1, wherein the TGF-beta signal inhibiting agent comprises at least one of 4-[4-(1,3-benzodioxol-5-yl)-5-(2-pyridinyl)-1H-imidazol-2-yl]benzamide, bone morphogenic protein (BMP)-7, anti-TGF-beta antibody, anti-TGF-beta receptor antibody, siRNA of TGF-beta, siRNA of a TGF-beta receptor, shRNA of TGF-beta, shRNA of a TGF-beta receptor, an aptamer of TGF-beta, an aptamer of a TGF-beta receptor, an antisense oligonucleotide of TGF-beta, 6,7-dimethoxy-2-((2E)-3-(1-methyl-2-phenyl-1H-pyrrolo[2,3-b]pyridin-3-yl-prop-2-enoyl))-1,2,3,4-tetrahydroisoquinolone, 3-(6-methyl-2-pyridinyl)-N-phenyl-4-(4-quinolinyl)-1H-pyrazole-1-carbothioamide, 2-(3-(6-methylpyridin-2-yl)-1H-pyrazol-4-yl)-1,5-naphthyridine, 6-(4-(piperidin-1-yl)ethoxy)phenyl)-3-(pyridin-4-yl)pyrazolo[1,5-a]pyrimidine, 2-(5-chloro-2-fluorophenyl)-4-[(4-pyridinyl)amino]pteridine, 4-[3-(2-pyridinyl)-1H-pyrazol-4-yl]-quinoline, pharmaceutically acceptable salts or solvates thereof, or solvates of the pharmaceutically acceptable salts.

5. The method according to claim 1, wherein the TGF-beta signal inhibiting agent comprises 4-[4-(1,3-benzodioxol-5-yl)-5-(2-pyridinyl)-1H-imidazol-2-yl]benzamide or a pharmaceutically acceptable salt thereof.

6. The method according to claim 1, wherein the subject a primate.

7. The method according to claim 1, wherein the subject a human.

8. The method according to claim 1, wherein the medicament comprises an additional medicinal component.

9. The method according to claim 1, wherein the medicament is eye-drops.

* * * * *